(12) United States Patent
Adams et al.

(10) Patent No.: US 6,515,015 B1
(45) Date of Patent: Feb. 4, 2003

(54) ANTIDIABETIC AGENTS BASED ON ARYL AND HETEROARYLACETIC ACIDS

(75) Inventors: Alan Adams, Cranford, NJ (US); Derek Von Langen, Fanwood, NJ (US); Hiroo Koyama, Hoboken, NJ (US); Richard Tolman, Los Altos, CA (US)

(73) Assignee: Merck & Co. Inc., Rahway, NJ (US)

( * ) Notice: Subject to any disclaimer, the term of this patent is extended or adjusted under 35 U.S.C. 154(b) by 5 days.

(21) Appl. No.: 09/695,009

(22) Filed: Oct. 24, 2000

Related U.S. Application Data

(62) Division of application No. 09/331,512, filed as application No. PCT/US97/23646 on Dec. 19, 1997, now Pat. No. 6,160,000.
(60) Provisional application No. 60/034,432, filed on Dec. 23, 1996, and provisional application No. 60/060,113, filed on Sep. 26, 1997.

(51) Int. Cl.$^7$ .................. A61K 31/343; A61K 31/34; C07D 307/80; C07D 307/92; C07D 407/12
(52) U.S. Cl. .................. 514/443; 514/469; 549/51; 549/469; 549/471
(58) Field of Search .................. 549/469, 471, 549/51; 514/443, 469

(56) References Cited

PUBLICATIONS

Dann et al., CA 98:53580, 1983.*

* cited by examiner

*Primary Examiner*—Laura L. Stockton
(74) *Attorney, Agent, or Firm*—James L. McGinnis; Melvin Winokur

(57) ABSTRACT

The instant invention is concerned with aryl and heteroaryl acetic acid and oxyacetic acid compounds, which are useful as antidiabetic compounds. Compositions and methods for their use in the treatment of diabetes and related diseases and for lowering triglyceride levels are disclosed.

23 Claims, No Drawings

ANTIDIABETIC AGENTS BASED ON ARYL AND HETEROARYLACETIC ACIDS

This is a division of application Ser. No. 09/331,512, filed Jun. 22, 1999, now U.S. Pat. No. 6,160,000, which was filed under 35 USC §371 as the national stage filing of PCT International Application No. PCT/US97/23646, filed Dec. 19, 1997, and claims priority from U.S. Provisional Application No. 60/034,432, filed Dec. 23, 1996, and No. 60/060,113, filed Sep. 26, 1997.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular disease, including nephropathy, neuropathy, retinopathy, hypertension, stroke, and heart disease. Therefore, glucose homeostasis is critically important for the treatment of diabetes.

Type I diabetes (IDDM) is associated with a deficiency of insulin. Type II, noninsulin dependent diabetes mellitus (NIDDM) is associated with a resistance to the stimulating or regulatory effect of insulin on glucose and lipid metabolism in the main insulin-sensitive tissues, namely, the muscle, liver and adipose tissue. This resistance to to the effect of insulin results in insufficient activation of glucose uptake, oxidation and storage in muscle, inadequate repression of lipolysis in adipose tissue and inadequate supression of glucose production and secretion in liver.

Standard treatments for NIDDM, which have not changed substantially in years, are all associated with limitations. Physical exercise and reduction in calorie intake improves the diabetic condition; however compliance is generally poor. Increasing the plasma level of insulin, either by administering an oral hypoglycemic such as a sulfonylurea (e.g. tolbutamide or glipizide) or by injecting insulin results in insulin levels which are sufficient to stimulate insulin-resistant tissues. However, low levels of plasma glucose and a heightened level of insulin resistance can result.

Thiazolidinediones (glitazones) were suggested to ameliorate many symptoms of NIDDM. These agents increase insulin sensitivity in muscle, liver and adipose tissue in several animal models of NIDDM, hopefully resulting in normalized levels of plasma glucose, triglycerides and non-esterified free fatty acids. However, serious undesirable effects have been observed, including cardiac hypertrophy, hemodilution and liver toxicity.

Hyperlipidemia is a condition that is characterized by an abnormally high level of serum lipids. This includes cholesterol, triglycerides and phospholipids. These lipids do not circulate freely in solution in plasma, but are bound to proteins and transported as macromolecular complexes called lipoproteins. See the *Merck Manual,* 16th Ed. 1992 (see for example pp. 1039–1040) and "Structure and Metabolism of Plasma Lipoproteins" in *Metabolic Basis of Inherited Disease,* 6th Ed. 1989, pp. 1129–1138. One form of hyperlipidemia is hypercholesterolemia, which is characterized by elevated LDL cholesterol levels. The initial treatment for hypercholesterolemia is often reduced dietary fat and cholesterol. Coupled with an appropriate exercise regimen, this can be an effective means by which to reduce hyperlipidemia. More typically, this means of lowering hyperlipidemia is insufficient, making drug therapy to reduce serum LDL-cholesterol more appropriate.

Although it is desirable to lower elevated levels of LDL cholesterol, it is also desirable to increase levels of HDL cholesterol, since increased levels of HDL are associated with a reduced risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid.

It is suggested that thiazolidinedione compounds exert their effects by binding to the peroxisome proliferator activated receptor (PPAR) family of receptors, controlling certain transcription elements having to do with the biological entities listed above. See Hulin et al., Current Pharm. Design (1996) 2, 85–102. Three sub-types of PPARs have been discovered and described: PPARα, PPARγ and PPARδ. PPARα is activated by a number of medium and long-chain fatty acids. It is involved in stimulating β-oxidation of fatty acids. PPARα is also activated by compounds known as fibric acid derivatives. These fibric acid derivatives, such as clofibrate, fenofibrate, bezafibrate, ciprofibrate, beclofibrate and etofibrate, as well as gemfibrozil reduce plasma triglycerides along with LDL cholesterol, and they are primarily used for the treatment of hypertriglyceridemia.

PPARγ receptor subtypes are involved in adipocyte differentiation. The DNA sequences for the PPARγ receptors are described in Elbrecht, et al., BBRC 224;431–437 (1996). Although peroxisome proliferators, including the fibrates and fatty acids, activate the transcriptional activity of PPARs, only prostaglandin $J_2$ derivatives have been identified as natural ligands of the PPARγ subtype, which also binds to thiazolidinedione antidiabetic agents with high affinity. The glitazones have been shown to bind to the PPARγ subtype.

The human nuclear receptor gene PPARδ (hPPARδ) has been cloned from a human osteosarcoma cell cDNA library and is fully described in A. Schmidt et al., *Molecular Endocrinology,* 6 :1634–1641 (1992), herein incorporated by reference. PPARδ is also referred as PPARβ and NUC1.

SUMMARY OF THE INVENTION

The present invention is directed to a compound represented by formula I or Ia:

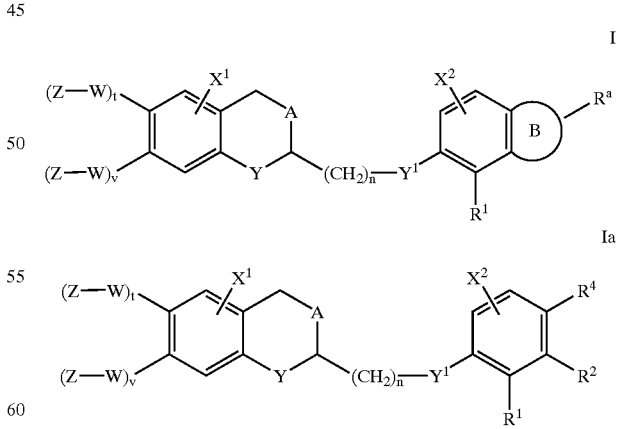

or a pharmaceutically acceptable salt thereof, wherein:

A is optionally a single or double bonded carbon or a single or double bond;

$R^1$ is selected from a group consisting of: H, $C_{1-5}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^2$ is selected from a group consisting of: H, $C_{1-15}$ alkyl, $C_{2-15}$ alkenyl, $OR^3$, $CO_2$alkyl, COalkyl, OH, —OC(O)$R^3$, $C_{2-15}$ alkynyl, $C_{5-10}$ aryl, $C_{5-10}$ heteroaryl, said alkyl, alkenyl, alkynyl, aryl and heteroaryl optionally substituted with 1 to 3 groups of $R^a$;

$R^3$ is selected from a group consisting of: H, $NHR^1$, NHacyl, $C_{1-15}$ alkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, alkenyl, alkynyl, aryl and heteroaryl optionally substituted with 1 to 3 groups of $R^a$;

$R^4$ is selected from the group consisting of: $R^2$, —D—$R^5$ or

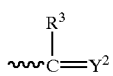

$R^5$ is selected from the group consisting of: $C_{5-10}$ aryl and $C_{5-10}$ heteroaryl, said aryl and heteroaryl optionally substituted with 1 to 3 groups of $R^a$;

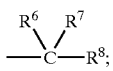

$R^8$ is selected from the group consisting of $CR^6R^7$, O, $NR^6$, and $S(O)_P$;

$R^6$ and $R^7$ are independently selected from the group consisting of H, $C_{1-6}$ alkyl;

B is a 5 or 6 membered heterocycle containing 0 to 2 double bonds, and 0 to 3 heteroatoms selected from the group consisting of O, S and N, the heteroatom being substituted at any position on the five or six membered heterocycle, the heterocycle being optionally unsubstituted or substituted with 1 to 3 groups of $R^a$;

D is selected from the group consisting of: O, S(O)p and $NR^1$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, aryl, heteroaryl, $CF_3$, $OCF_3$, —O—, CN, $NO_2$, $R^3$, $OR^3$; $SR^3$, $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or C1–6 alkyl;

Y is selected from the group consisting of: $S(O)_p$, —$CH_2$—, CO, $NR^1$, O, $SO_2NH$, $NHSO_2$;

$Y^2$ is selected from the group consisting of: O, $N(C_{1-15})$ alkyl, $N(CO_2)$alkyl, N—Oalkyl, N—Oacyl and N—OH, with the proviso that if $Y^2$ is O and $R^3$ is $CH_3$ then n is 2;

$Y^1$ is selected from the group consisting of: O, NH, $S(O)_p$ and C;

Z is selected from the group consisting of: $CO_2R^3$, $R^3CO_2R^3$, $CONHSO_2Me$, $CONH_2$ and 5-(1H-tetrazole); or $(Z—W)_t$ or $(Z—W)_v$ together with $X^1$ can form a 5 or 6 membered ring, said ring being a carbocycle, aryl or heteroaryl and optionally substituted with 1 to 3 groups of $R^a$; in the case where $(Z—W)_t$ is used v is 0 or 1; in the case where $(Z—W)_v$ is used t is 0 or 1;

t and v are independently 0 or 1 such that t+v=1;

n is 2–4 and p is 0–2.

Also included in the invention is a pharmaceutical composition which is comprised of a compound of formula I or Ia in combination with a pharmaceutically acceptable carrier.

Also included in the invention is a pharmaceutical composition which is comprised of a compound of formula I or Ia in combination with one or more known sulfonylureas, biguanides, α-glucosidase inhibitors, other insulin secretogogues or insulin.

Also included in the invention is a method for raising high density lipoprotein (HDL) plasma levels in a mammal in need of such treatment comprising administering an effective amount of a compound of formula I or Ia.

Also included in the invention is a method for preventing, halting, slowing or otherwise treating the progression of atherosclerotic cardiovascular diseases and related conditions and disease events in a mammal in need of such treatment comprising administering an effective amount of a compound of formula I or Ia.

Also included in the invention is a method for preventing, halting or slowing the progression of atherosclerotic cardiovascular diseases and related conditions and disease events in a mammal in need of such treatment comprising administering an effective amount of a compound of formula I or Ia in combination with one or more active agents such as antihyperlipidemic agents, HMG-CoA synthase inhibitors, squalene epoxidase inhibitors and the like.

Also included in the invention is a method of treating or controlling diabetes and related diseases such as diabetic retinopathy, diabetic nephropathy and the like, which comprises administering to a mammalian diabetic patient an effective amount of a compound of formula I or Ia.

Also included in the invention is a method of treating or controlling diabetes and related diseases such as diabetic retinopathy; diabetic nephropathy and the like, which comprises administering a compound of formula I or Ia in combination with one or more known sulfonylureas, biguanides, α-glucosidase inhibitors, other insulin secretogogues or insulin.

Also included in the present invention is a method of treating pancreatitis in a mammalian patient in need of such treatment, which is comprised of administering to said patient an amount of a compound of formula I or Ia which is effective for treating pancreatitis.

DESCRIPTION OF THE INVENTION

The invention is described herein in detail using the terms defined below unless otherwise specified.

The term "alkyl" and the alkyl portion of "acyl" refer to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

The carbon chain of "acyl" also includes alkenyl and alkynyl groups as described below, with the double or triple bonds being located in appropriate positions within the chain.

Alkyl also includes a straight or branched alkyl group which contains or is interrupted by a cycloalkylene portion. Examples include the following:

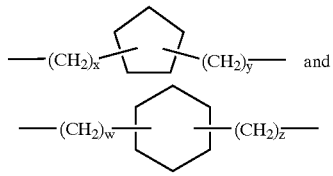

wherein: x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated carbon length in either a straight or branched configuration attached through an oxygen linkage and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propargyloxy, and the like.

The term halo as used herein, represents fluoro, chloro, bromo or iodo.

Aryl refers to aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 0–3 groups selected from $R^a$. The preferred aryl groups are phenyl and naphthyl. Aryl groups may likewise be substituted as defined below. Preferred substituted aryls include phenyl and naphthyl substituted with zero or three groups of $R^a$.

Heteroaryl is a group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups; examples of heteroaryls are pyridyl, quinolyl, purinyl, imidazolyl, imidazopyridyl and pyrimidinyl.

A subset of compounds of the invention is included herein and described in connection with formula I or Ia:

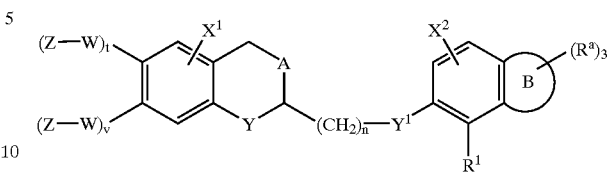

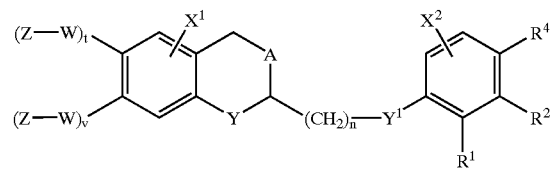

as well as pharmaceutically acceptable salts thereof, wherein:
A represents a single or double bonded carbon, or a direct single or double bond;
Y represents a member selected from the group consisting of: —S(O)$_p$— wherein p is 0, 1 or 2, —CH$_2$—, —C(O)—, —NR$^1$—, —O—, —SO$_2$NH— and —NHSO$_2$—;
one of t and v is zero and the other is 1;
W is

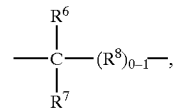

and
Z is selected from the group consisting of: CO$_2$R$^{3'}$, CONHSO$_2$C$_{1-6}$ alkyl, CONH$_2$ and 5-(1H-tetrazolyl); or in the alternative,
one of (Z—W)$_t$ and (Z—W)$_v$ is taken in combination with X$^1$ to represent a 5 or 6 membered fused ring, said ring being a carbocycle, aryl or heteroaryl ring, and being optionally substituted with 1 to 3 R$^a$ groups;
when (Z—W)$_t$ is taken in combination with X$^1$, v is 0 or 1, and when (Z—W)$_v$ is taken in combination with X$^1$, t is 0 or 1;
X$^1$ and X$^2$ are independently selected from a group consisting of: H, OH, C$_{1-15}$ alkyl, C$_{2-15}$ alkenyl, C$_{2-15}$ alkynyl, halo, C$_{5-10}$ aryl, C$_{5-10}$ heteroaryl, C$_{1-10}$ acyl, C$_{1-5}$ alkoxy, C$_{5-10}$ aryloxy, C$_{2-15}$ alkenyloxy, C$_{2-15}$ alkynyloxy, heteroaryloxy, C$_{1-10}$ acyloxy
said alkyl, alkenyl, alkynyl, aryl, acyl and heteroaryl, and the alkyl, alkenyl, alkynyl, aryl acyl and heteroaryl portions of alkoxy, aryloxy, alkenyloxy, alkynyloxy, heteroaryloxy and acyloxy being optionally substituted with 1 to 3 R$^a$ groups;
n is 2, 3 or 4;
Y$^1$ represents O, NH, CH$_2$ or S(O)$_p$ wherein p is as defined above;
B represents a 5 or 6 membered fused ring containing 0 to 2 double bonds, and optionally containing 1 to 3 heteroatoms selected from the group consisting of O, S and N, said ring being optionally substituted with 1 to 3 R$^a$ groups;
R$^1$ is selected from a group consisting of: H, C$_{1-15}$ alkyl, C$_{2-15}$ alkenyl and C$_{2-15}$ alkynyl, said alkyl, alkenyl and alkynyl being optionally substituted with 1 to 3 R$^a$ groups;

$R^2$ is selected from a group consisting of: H, OH, $C_{1-15}$ alkyl, $C_{2-15}$ alkenyl, $C_{2-15}$ alkynyl, $C_{5-10}$ aryl, $C_{5-10}$ heteroaryl, —$C(O)C_{1-15}$ alkyl, $CO_2C_{1-6}$ alkyl, —OC(O)$R^{3'}$, $C_{1-6}$ alkoxy, $C_{5-10}$ aryloxy, $C_{2-15}$ alkenyloxy, $C_{2-15}$ alkynyloxy, heteroaryloxy and $C_{1-10}$ acyloxy, said alkyl, alkenyl, alkynyl, aryl and heteroaryl, and the alkyl, aryl, alkenyl, alkynyl heteroaryl and acyl portions of alkoxy, aryloxy, alkenyloxy, alkynyloxy, heteroaryloxy and acyloxy being optionally substituted with 1 to 3 $R^a$ groups;

$R^3$ is selected from a group consisting of: H, OH, $NHR^1$, NHacyl, $C_{1-15}$ alkyl, $C_{2-15}$ alkenyl, $C_{1-15}$ alkoxy, $CO_2$alkyl, $C_{2-15}$ alkynyl, $C_{5-10}$ aryl, and $C_{5-10}$ heteroaryl said alkyl, alkenyl, alkynyl, aryl and heteroaryl optionally substituted with 1 to 3 $R^a$ groups;

each $R^a$ independently represents a member selected from the group consisting of: $R^{3'}$, halo, $CF_3$, $OCF_3$, CN, $NO_2$, $OR^{3'}$, $S(O)_p$—$R^{3'}$; $N(R^{3'})_2$, $NR^{3'}COR^{3'}$, $NR^{3'}CO_2R^{3'}$, $NR^{3'}CON(R^{3'})_2$, $NR^{3'}SO_2R^{3'}$, $C(O)R^{3'}$, $CO_2R^{3'}$, $CON(R^{3'})_2$, $SO_2N(R^{3'})_2$, $OCON(R^{3'})_2$, and when $R^{3'}$ is present and represents alkyl, alkenyl, alkynyl, aryl or heteroaryl, said alkyl, alkenyl, alkynyl, aryl or heteroaryl group is optionally substituted with 1 to 3 halo, hydroxy, $C_{1-3}$ alkoxy, carboxy or amino groups, and when at least two $R^a$ groups are present, they may also be taken in combination with any intervening atoms to represent a 4–6 membered ring, said ring containing 0–3 heteroatoms selected from O, $S(O)_p$ and N, and said ring being optionally interrupted by 1–2 —C(O)— groups, and optionally substituted with 1–3 halo, hydroxy, $C_{1-6}$ alkyl or amino groups;

$R^{3'}$ represents H, $C_{1-6}$ alkyl, $C_{2-6}$ alkenyl, $C_{2-6}$ alkynyl, aryl or heteroaryl;

$R^4$ represents $R^2$, —D—$R^5$ or

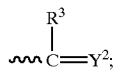

D is selected from O, S(O)p, $NR^1$ and $CR^6R^7$;

$R^5$ is selected from the group consisting of: $C_{5-10}$ aryl and $C_{5-10}$ heteroaryl, said aryl and heteroaryl being optionally substituted with 1 to 3 $R^a$ groups;

$Y^2$ is selected from the group consisting of: O, $N(C_{1-15})$ alkyl, $N(CO_2)$alkyl, N—Oalkyl, N—Oacyl and N—OH, with the proviso that if $Y^2$ is O and $R^3$ is $CH_3$ then n is 2;

$R^8$ is optional and is selected from the group consisting of $CR^6R^7$, O, $NR^6$ and $S(O)_p$, and $R^6$ and $R^7$ are independently selected from H and $C_{1-6}$ alkyl.

One embodiment of the invention which is particular interest is realized when Y is O and all other variables are as described above.

Another embodiment of the invention is realized when Y is $S(O)_p$, p is 0–2 and all other variables are described as above.

Still another embodiment of the invention is realized when Y is —$CH_2$— and all other variables are described as above.

Yet another embodiment of the invention is realized when Y is CO and all other variables are described as above.

A further embodiment of the invention is realized when Y is NH and all other variables are described as above.

Another embodiment of the invention is realized when Y is $NHSO_2$ or $SO_2NH$ and all other variables are described as above.

Another embodiment of the invention is realized when (Z—W)$_t$ or (Z—W)$_v$ together with $X^1$ form a 5 or 6 membered ring, said ring being a carbocycle, aryl or heteroaryl and optionally substituted with 1 to 3 $R^a$ groups. In the case where (Z—W)$_t$ is used, v is 0 or 1; in the case where (Z—W)$_v$ is used, t is 0 or 1; and all other variables are described as above.

Another embodiment of the novel compounds of the instant invention is realized when A is a single or double bonded carbon and all other variables are described as above.

Still another embodiment of the novel compounds of the instant invention is realized when A is a single or double bond and all other variables are described as above.

Still another embodiment of the invention is realized when B is a 5 or 6 membered heterocycle containing 0 to 2 double bonds, and 1 to 3 heteroatoms selected from the group consisting of O, S and N, the heteroatom being present at any position in the five or six membered ring, the heterocycle being unsubstituted or substituted with 1 to 3 $R^a$ groups, and all other variables are described as above.

Still another embodiment of the novel compounds of the instant invention is realized when $R^4$ is selected from the group consisting of: $R^2$, —D—$R^5$ and

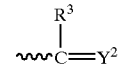

and all other variables are described as above. Preferably $R^4$ represents $R^2$ or —D—$R^5$.

A preferred embodiment of the invention is realized when:

$R^1$ is H or $C_{1-5}$ alkyl;

$X^1$ and $X^2$ are independently H or halo;

B is a 5 or 6 membered heterocycle containing 0 to 2 double bonds, and 1 to 3 heteroatoms selected from the group consisting of O, S and N, the heteroatom being at any allowable position in the five or six membered heterocycle, the heterocycle being unsubstituted or substituted with 1 to 3 $R^a$ groups;

Y is O, NH or S;

$Y^1$ is O;

W is —$CR^6R^7$—;

$R^a$ is a member selected from the group consisting of: halo, aryl, heteroaryl, $CF_3$, $OCF_3$, —O—, CN, $NO_2$, $R^{3'}$, $OR^{3'}$; $SR^{3'}$, $S(O)R^{3'}$, $SO_2R^{3'}$, $NR^{3'}COR^{3'}$, $COR^{3'}$, $CON(R^{3'})_2$, $SO_2N(R^{3'})_2$, said aryl and heteroaryl optionally substituted with 1 to 3 halo or C1–6 alkyl groups; and Z is $CO_2R^{3'}$, $CONHSO_2Me$, $CONH_2$ or 5-(1H-tetrazolyl).

All other variables are as originally defined.

Another preferred embodiment of the invention is realized when:

$R^1$ is H or $C_{1-5}$ alkyl;

$R^4$ is $R^2$, —D—$R^5$ or

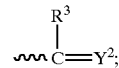

$X^1$ and $X^2$ are independently H or halo;

Y is O, NH or S;

$Y^1$ is O;

W is —$CR^6R^7$—;

$R^a$ is a member selected from the group consisting of: halo, aryl, heteroaryl, $CF_3$, $OCF_3$, —O—, CN, $NO_2$, $R^{3'}$, $OR^{3'}$; $SR^{3'}$, $S(O)R^{3'}$, $SO_2R^{3'}$, $NR^{3'}COR^{3'}$, $COR^{3'}$, $CON(R^{3'})_2$, $SO_2N(R^{3'})_2$, wherein $R^{3'}$ represents H, $C_{1-6}$ alkyl, $C_{2-6}$ alkenyl, $C_{2-6}$ alkynyl, aryl or heteroaryl, said aryl and heteroaryl optionally substituted with 1 to 3 groups of halo or $C_{1-6}$ alkyl; and Z is $CO_2R^{3'}$, $CONHSO_2Me$, $CONH_2$ or 5-(1H-tetrazolyl).

Still another preferred embodiment of the invention is realized when:

$R^1$ is $C_{1-15}$ alkyl;

$R^4$ is —D—$R^5$ or

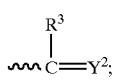

$X^2$ is H, or halo;

Y is O, NH or S;

$Y^1$ is O;

$R^a$ is a member selected from the group consisting of: halo, aryl, heteroaryl, $CF_3$, $OCF_3$, —O—, CN, $NO_2$, $R^{3'}$, $OR^{3'}$; $SR^{3'}$, $S(O)R^{3'}$, $SO_2R^{3'}$, $NR^{3'}COR^{3'}$, $COR^{3'}$, $CON(R^{3'})_2$, $SO_2N(R^{3'})_2$, said aryl and heteroaryl optionally substituted with 1 to 3 halo or $C_{1-6}$ alkyl groups;

$R^{3'}$ represents H, $C_{1-6}$ alkyl, $C_{2-6}$ alkenyl, $C_{2-6}$ alkynyl, aryl or heteroaryl, said aryl and heteroaryl optionally substituted with 1 to 3 halo or $C_{1-6}$ alkyl groups;

(Z—W)$_t$ or (Z—W)$_v$ together with $X^1$ forms a 5 or 6 membered ring, said ring being a carbocycle, aryl or heteroaryl and optionally substituted with 1 to 3 $R^a$ groups; in the case where (Z—W)$_t$ is used v is 0 or 1; in the case where (Z—W)$_v$ is used t is 0 or 1; and all other variables are described as above.

Examples of compounds of the invention include the following:

2-(2-(3-Phenyl-7-propylbenzofuran-6-yloxy)ethyl)-indole-5-acetic acid;

2-(2-(3-(2,2-Dimethylpropyl)-7-propylbenz[4,5]isoxazol-6-yloxy)ethyl)indole-5-acetic acid;

2-(2-(3-Phenyl-7-propylbenz[4,5]isoxazol-6-yloxy)ethyl) indole-5-acetic acid;

2-(2-(3-Neopentyl-7-propylbenzofuran-6-yloxy)ethyl)-indole-5-(2,2-dimethyl)acetic acid;

2-(2-(3-Phenyl-7-propylbenz[4,5]isoxazol-6-yloxy)ethyl)-indole-5-propan-3-oic acid;

2-(2-(3-Neopentyl-7-propylbenz[4,5]isoxazol-6-yloxy) ethyl)-indole-5-propan-3-oic acid;

2-(2-(3-Phenyl-7-propylbenzofuran-6-yloxy)ethyl)-indole-5-oxyacetic acid;

2-(2-(3-Neopentyl-7-propylbenzofuran-6-yloxy)ethyl)-indole-5-oxyacetic acid;

N-[2-(2-(3-Phenyl-7-propylbenz[4,5]isoxazol-6-yloxy) ethyl)-indol-5-yl]glycine;

N-[2-(2-(3-Neopentyl-7-propylbenz[4,5]isoxazol-6-yloxy) ethyl)-indol-5-yl]glycine;

2-(2-(3-Phenyl-7-propylbenzofuran-6-yloxy)ethyl)-indole-6-acetic acid;

2-(2-(3-Neopentyl-7-propylbenzofuran-6-yloxy)ethyl)-indole-6-acetic acid;

2-(2-(3-Phenyl-7-propylbenz[4,5]isoxazol-6-yloxy)ethyl)-4-chloroindole-5-acetic acid;

2-(2-(3-Neopentyl-7-propylbenz[4,5]isoxazol-6-yloxy) ethyl)-4-chloroindole-5-acetic acid;

2-(2-(3-Phenyl-7-propylbenzofuran-6-yloxy)ethyl)-quinolin-6-acetic acid;

2-(2-(3-Neopentyl-7-propylbenzofuran-6-yloxy)ethyl)-quinolin-6-acetic acid;

2-(2-(3-Phenyl-7-propylbenz[4,5]isoxazol-6-yloxy)ethyl)-quinolin-7-acetic acid;

2-(2-(3-Neopentyl7-propylbenz[4,5]isoxazol-6-yloxy) ethyl)-quinolin-7-acetic acid;

2-(2-(3-Phenyl-7-propylbenzofuran-6-yloxy)ethyl)-quinazolin-6-acetic acid;

2-(2-(3-Neopentyl-7-propylbenzofuran-6-yloxy)ethyl)-quinazolin-6-acetic acid;

2-(2-(3-Phenyl-7-propylbenz[4,5]isoxazol-6-yloxy)ethyl)-quinazolin-7-acetic acid;

2-(2-(3-Neopentyl-7-propylbenz[4,5]isoxazol-6-yloxy) ethyl)-quinazolin-7-acetic acid;

2-(2-(3-Phenyl-7-propylbenzofuran-6-yloxy)ethyl)-3-methylindole-5-acetic acid;

2-(2-(3-Neopentyl-7-propylbenzofuran-6-yloxy)ethyl)-3-methylindole-5-acetic acid;

2-(2-(3-Phenyl-7-propylbenz[4,5]isoxazol-6-yloxy)ethyl)-3-butylindole-5-acetic acid;

2-(2-(3-Neopentyl-7-propylbenz[4,5]isoxazol-6-yloxy) ethyl)-3-butylindole-5-acetic acid;

2-(2-(3-Phenyl-7-propylbenzofuran-6-yloxy)ethyl)-7-propylindole-5-acetic acid;

2-(2-(3-Neopentyl-7-propylbenzofuran-6-yloxy)ethyl)-7-propylindole-5-acetic acid;

2-(2-(3-Phenyl-7-propylbenz[4,5]isoxazol-6-yloxy)ethyl)-N-methylindole-5-acetic acid;

2-(2-(3-Neopentyl-7-propylbenz[4,5]isoxazol-6-yloxy) ethyl)-N-methylindole-5-acetic acid;

2-(3-(3-Phenyl-7-propylbenzofuran-6-yloxy)propy)indole-5-acetic acid;

2-(3-(3-Neopentyl-7-propylbenzofuran-6-yloxy)propy) indole-5-acetic acid;

2-(2-(3-Phenyl-7-propylbenz[4,5]isoxazol-6-yloxy)propyl) indole-5-acetic acid;

2-(2-(3-Neopentyl-7-propylbenz[4,5]isoxazol-6-yloxy) propyl)indole-5-acetic acid;

2-(2-(3-Phenyl-7-(cyclopropylmethyl)benzofuran-6-yloxy) ethyl)indole-5-acetic acid;

2-(2-(3-Neopentyl-7-(cyclopropylmethyl)benzofuran-6-yloxy)ethyl)indole-5-acetic acid;

2-(2-(1-Phenyl-4-propylindol-5-yloxy)ethyl)indole-5-acetic acid;

2-(2-(1-Phenyl-4-propylindol-5-yloxy)ethyl)benzofuran-5-acetic acid;

2-(2-(1-Phenyl-4-propylindol-5-yloxy)ethyl)indole-5-oxyacetic acid;

2-(2-(1-Phenyl-4-propylindol-5-yloxy)ethyl)indole-5-propan-3-oic acid;

2-(2-(4-Phenoxy-3-propylphenoxy)ethyl)indole-5-acetic acid;

2-(2-(4-(4-Tolyloxy)-3-propylphenoxy)ethyl)indole-5-acetic acid;

2-(2-(4-Valeryl-3-propylphenoxy)ethyl)indole-5-acetic acid;

2-(2-(4-Benzoyl-3-propylphenoxy)ethyl)indole-5-acetic acid;

2-(2-(4-(N-Hydroxyimino)valeryl-3-propylphenoxy)ethyl) indole-5-acetic acid;

2-(2-(4-(N-Hydroxyimino)benzoyl-3-propylphenoxy)ethyl) indole-5-acetic acid;

2-(2-(3-(3-Fluorophenyl)-7-propylbenzofuran-6-yloxy) ethyl)indole-5-acetic acid;

2-(2-(3-(Phen-2-ethyl)-7-propylbenzofuran-6-yloxy)ethyl)
    indole-5-acetic acid;
2-(2-(3-(4-t-Butylphenyl)-7-propylbenz[4,5]isoxazol-6-
    yloxy)ethyl)indole-5-acetic acid;
2-(2-(3-(2,2-Dimethyl-2-phenylethyl)-7-propylbenz[4,5]
    isoxazol-6-yloxy)ethyl)indole-5-acetic acid;
2-(2-(4-Phenoxy-2-propylphenoxy)ethyl)indole-5-acetic
    acid sodium salt;
2-(2-(4-Phenoxy-2-propylphenoxy)ethyl)indole-5-acetic
    acid;
2-(2-(4-Phenoxy-2-propylphenoxy)ethyl)indole-5-acetic
    acid methyl ester;
2-(2-(3-(2-Phenyl)ethyl-7-(n-propyl)benz[4,5]isoxazol-6-
    yloxy)ethyl)indole-5-acetic acid;
2-(2-(4-Phenoxy-2-propylphenoxy)ethyl)benzofuran-5-
    acetic acid;
2-(2-(3-(2,2-Dimethylpropyl)-7-(n-propyl)benz[4,5]
    isoxazol-6-yloxy)ethyl)benzofuran-5-acetic acid;
2-(2-(3-Phenyl-7-(n-propyl)benz[4,5]isoxazol-6-yloxy)
    ethyl)benzofuran-5-acetic acid;
2-(2-(3-Phenyl-7-(n-propyl)benzofuran-6-yloxy)ethyl)-
    benzofuran-5-acetic acid;
2-(2-(4-Phenoxy-2-propylphenoxy)ethyl-6,7,8,9-
    tetrahydronaphtho[2,1-b]furan-7-carboxylic acid sodium
    salt;
2-(2-(3-Phenyl-7-(n-propyl)benz[4,5]isoxazol-6-yloxy)
    ethyl)-6,7,8,9-tetrahydronaphtho[2,1-b]furan-7-
    carboxylic acid; and
2-(2-(3-(2,2-Dimethylpropyl)-7-(n-propyl)benz[4,5]
    isoxazol-6-yloxy)ethyl)-6,7,8,9-tetrahydronaphtho[2,1-b]
    furan-7-carboxylic acid.
Preferred examples of the compounds of the invention are
as follows:
2-(2-(3-Phenyl-7-propylbenzofuran-6-yloxy)ethyl)indole-5-
    acetic acid;
2-(2-(3-Neopentyl-7-propylbenzofuran-6-yloxy)ethyl)
    indole-5-acetic acid;
2-(2-(3-Phenyl-7-propylbenzisoxazol-6-yloxy)ethyl)indole-
    5-acetic acid;
2-(2-(3-Neopentyl-7-propylbenzisoxazol-6-yloxy)ethyl)
    indole-5-acetic acid;
2-(2-(3-Phenyl-7-propylbenzofuran-6-yloxy)ethyl)
    benzothiophen-5-acetic acid;
2-(2-(3-Neopentyl-7-propylbenzofuran-6-yloxy)ethyl)
    benzofuran-5-acetic acid;
2-(2-(3-Phenyl-7-propylbenzisoxazol-6-yloxy)ethyl)
    benzofuran-5-acetic acid;
2-(2-(3-Neopentyl-7-propylbenzisoxazol-6-yloxy)ethyl)
    benzothiophen-5-acetic acid;
2-(2-(4-Phenoxy-2-propylphenoxy)ethyl)indole-5-acetic
    acid;
2-(2-(4-Phenoxy-2-propylphenoxy)ethyl)indole-5-acetic
    acid methyl ester;
2-(2-(3-(2-Phenyl)ethyl-7-(n-propyl)benz[4,5]isoxazol-6-
    yloxy)ethyl)indole-5-acetic acid;
2-(2-(4-Phenoxy-2-propylphenoxy)ethyl)benzofuran-5-
    acetic acid;
2-(2-(3-(2,2-Dimethylpropyl)-7-(n-propyl)benz[4,5]
    isoxazol-6-yloxy)ethyl)benzofuran-5-acetic acid;
2-(2-(3-Phenyl-7-(n-propyl)benz[4,5]isoxazol-6-yloxy)
    ethyl)benzofuran-5-acetic acid;
2-(2-(3-Phenyl-7-(n-propyl)benzofuran-6-yloxy)ethyl)-
    benzofuran-5-acetic acid;
2-(2-(4-Phenoxy-2-propylphenoxy)ethyl-6,7,8,9-
    tetrahydronaphtho[2,1-b]furan-7-carboxylic acid sodium
    salt;
2-(2-(3-Phenyl-7-(n-propyl)benz[4,5]isoxazol-6-yloxy)
    ethyl)-6,7,8,9-tetrahydronaphtho[2,1-b]furan-7-
    carboxylic acid; and
2-(2-(3-(2,2-Dimethylpropyl)-7-(n-propyl)benz[4,5]
    isoxazol-6-yloxy)ethyl)-6,7,8,9-tetrahydronaphtho[2,1-b]
    furan-7-carboxylic acid.
More preferred compounds are as follows:
2-(2-(4-Phenoxy-2-propylphenoxy)ethyl)indole-5-acetic
    acid;
2-(2-(4-Phenoxy-2-propylphenoxy)ethyl)indole-5-acetic
    acid methyl ester;
2-(2-(3-(2-Phenyl)ethyl-7-(n-propyl)benz[4,5]isoxazol-6-
    yloxy)ethyl)indole-5-acetic acid and
2-(2-(4-Phenoxy-2-propylphenoxy)ethyl-6,7,8,9-
    tetrahydronaphtho[2,1-b]furan-7-carboxylic acid sodium
    salt.

The compounds of the present invention may have asymmetric centers and occur as racemates, racemic mixtures, and as individual diastereomers, with all possible isomers, including optical isomers, being included in the present invention.

Compounds of the general Formula I or Ia may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties. They are useful in treating or preventing diabetes and related diseases such as diabetic retinopathy, diabetic nephropathy and the like, treating obesity, lowering triglyceride levels and preventing vascular restenosis, and treating pancreatitis. They are useful in treating other disorders where insulin resistance is a component including ovarian hyperandrogenism (polycyctic ovarian syndrome). They are also useful in raising high density lipoprotein levels, preventing, halting or slowing the progression of atherosclerotic cardiovascular diseases and related conditions and disease events.

The present invention further provides a compound of the general Formula I or Ia, or a pharmaceutically acceptable salt or ester thereof, for use in the treatment of hyperglycemia (diabetes) in human or non-human animals.

The present invention further provides a compound of the general Formula I or Ia, or a pharmaceutically acceptable salt or ester thereof, in combination with sulfonylureas, biguanides, α glucosidase inhibitors, other insulin secretogogue or insulin for use in the treatment of diabetes and related diseases such as diabetic retinopathy; diabetic nephropathy and the like; pancreatitis; obesity, lowering triglyceride levels, vascular restenosis, other disorders where insulin resistance is a component, such as ovarian hyperandrogenism (polycyctic ovarian syndrome), raising high density lipoprotein levels, and preventing, halting or slowing the progression of atherosclerotic cardiovascular diseases and related conditions and disease events and hypertension in human or non-human animals.

In one aspect, the present invention provides a compound of Formula I or Ia for use in the treatment of obesity in human or non-human animals. Said compound can be effectively used in combination with other known or proposed strategies for the treatment of obesity or obesity-related disorders; for example, fenfluramine, dexfenfluramine, phentermine and $\beta_3$ adrenergic receptor agonist agents.

Diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies. The instant compounds can be effectively used alone as well as in combination with known therapies for diabetes including insulin, sulfonylureas, biguanides (such as metformin), α-glucosidase inhibitors (such as acarbose) and others.

Two major forms of diabetes mellitus are now recognized. Type I diabetes, or insulin-dependent diabetes, is the result of a deficiency of insulin, the hormone which regulates glucose utilization. Type II diabetes, or non-insulin dependent diabetes, often occurs in the face of normal, or even elevated levels of insulin and appears to be the result of the inability of tissue to respond appropriately to insulin. Most Type II diabetics are also obese. Accordingly, an aspect the present invention provides a method of lowering triglyceride levels which comprises administering, to a mammal in need thereof, a therapeutically effective amount of a compound of the formula I or Ia or pharmaceutically acceptable salt or ester thereof.

In addition the compounds of the present invention lower or modulate triglyceride levels and/or cholesterol levels and raise HDL plasma levels and are therefore of use in treating medical conditions wherein such lowering (and raising) is thought to be beneficial. Thus they may be used in the treatment of hypertension, obesity, atherosclerotic disease events, diabetes and related conditions by administering to a mammal in need of such treatment, a therapeutically effective amount of a compound of formula I or Ia or a pharmaceutically acceptable salt thereof.

The compositions are comprised of a compound of formula I or Ia in combination with a carrier. They may also contain other active ingredients known for use in the treatment of atherosclerotic disease events, diabetes, hypertension, obesity and related conditions, for example, fibrates such as clofibrate, bezafibrate and gemfibrozil; inhibitors of cholesterol biosynthesis, such as HMG-CoA reductase inhibitors, for example, lovastatin, simvastatin and pravastatin; inhibitors of cholesterol absorption, for example, beta-sitosterol, and (acyl CoA:cholesterol acyltransferase) inhibitors, for example, melinamide; anion exchange resins, for example, cholestyramine, colestipol or a dialkylaminoalkyl derivatives of a cross-linked dextran; nicotinyl alcohol, nicotinic acid or a salt thereof; vitamin E; and thyromimetics.

In particular the invention provides methods for preventing or reducing the risk of developing atherosclerosis, comprising the administration of a prophylactically effective amount of a compound of formula I or Ia alone or in combination with one or more additional pharmaceutically active agents, to a mammal, particularly human, who is at risk of developing atherosclerosis.

Atherosclerosis as used herein encompasses vascular diseases and conditions that are recognized and understood by practicing physicians. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The instant invention further provides methods for preventing or reducing the risk of a first or subsequent (where the potential exists for recurrence) atherosclerotic disease event, comprising the administration of a prophylactically effective amount, or more particularly, an anti-atherosclerotic effective amount of cholesterol biosynthesis inhibitor, of a compound of formula I or Ia alone or in combination with one or more additional pharmaceutically active agents, to a mammal, particularly human, who is at risk for having an atherosclerotic disease event. The term "atherosclerotic disease event" as used herein is intended to encompass coronary heart disease events, cerebrovascular events, and intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. It is intended that persons who have previously experienced one or more non-fatal atherosclerotic disease event are those for whom the potential for recurrence of such an event exists.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, high levels of low density lipoprotein cholesterol, and a family history of atherosclerotic cardiovascular disease. Published guidelines for determining those who are at risk of developing atherosclerotic disease can be found in: National Cholesterol Education Program, Second report of the Expert Panel on *Detection, Evaluation, and Treatment of High Blood Cholesterol in Adults (Adult Treatment Panel II)*, National Institute of Health, National Heart Lung and Blood Institute, NIH Publication No. 93-3095, September 1993; abbreviated version: Expert Panel on Detection, Evaluation, and Treatment of High Blood Cholesterol in Adults, *Summary of the second report of the national cholesterol education program (NCEP) Expert Panel on Detection, Evaluation, and Treatment of High Blood Cholesterol in Adults (Adult Treatment Panel II), JAMA,* 1993, 269, pp. 3015–23. People identified as having one or more of the above-noted risk factors, as well as people who already have atherosclerosis, are intended to be included within the group of people considered to be at risk for having an atherosclerotic disease event.

The compounds of the present invention may be orally administered as a pharmaceutical composition, for example, with an inert diluent, or with an edible carrier, or they may be enclosed in hard or soft shell capsules, or they may be compressed into tablets, or incorporated directly into food. For oral therapeutic administration, which includes sublingual administration, these active compounds may be incorporated with excipients and used in the form of tablets, capsules, ampules, sachets, elixirs, suspensions, syrups and the like. Such compositions and preparations may contain, e.g., at least about 0.1 percent of active compound. The percentage of active compound in these compositions may, of course, be varied and may conveniently be between about 2 percent to about 90 percent of the weight of the unit. The active compounds can also be administered intranasally as, for example, liquid drops or spray.

The effective dosage of active ingredient employed may vary depending on the particular compound employed, the mode of administration, the condition being treated and the severity of the condition.

When treating or preventing diabetes mellitus and/or hyperglycemia or hypertriglyceridemia, or obesity, or when treating, preventing or slowing the progression of atherosclerosis, generally satisfactory results are obtained when the compounds are administered at a daily dosage of from about 0.1 milligram to about 100 milligrams per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

The compounds of the instant invention may be used effectively alone or in combination with one or more additional active agents depending on the desired target therapy. Combination therapy includes administration of a single pharmaceutical dosage formulation which contains a compound of formula I or Ia and one or more additional active agents, as well as administration of a compound of formula I or Ia and each active agent in its own separate pharmaceutical dosage formulation. For example, a compound of formula I or Ia and an HMG-CoA reductase inhibitor can be administered to the patient together in a single oral dosage composition such as a tablet or capsule, or each agent administered in separate oral dosage formulations. Where separate dosage formulations are used, a compound of formual I or Ia and one or more additional active agents can be administered at essentially the same time, i.e., concurrently, or at staggered times, i.e, sequentially. Combination therapy is understood to include all these regimens.

An example of combination treatment or prevention of atherosclerosis may be wherein a compound of formula I or Ia is administered in combination with one or more of the following active agents: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor such as melinamide; probucol; nicotinic acid and the salts thereof and niacinamide; a cholesterol absorption inhibitor such as beta-sitosterol; a bile acid sequestrant anion exchange resin such as cholestyramine, colestipol or dialkylaminoalkyl derivatives of a cross-linked dextran; an LDL (low density lipoprotein) receptor inducer; fibrates such as clofibrate, bezafibrate, fenofibrate, and gemfibrizol; vitamin $B_6$ (also known as pyridoxine) and the pharmaceutically acceptable salts thereof such as the HCl salt; vitamin $B_{12}$ (also known as cyanocobalamin); anti-oxidant vitamins such as vitamin C and E and beta carotene; a beta-blocker; an angiotensin II antagonist; an angiotensin converting enzyme inhibitor; and a platelet aggregation inhibitor such as fibrinogen receptor antagonists (i.e., glycoprotein IIb/IIIa fibrinogen receptor antagonists) and aspirin. As noted above, the compounds of formula I or Ia can be administered in combination with more than one additional active agent, for example, a combination of a compound of formula I or Ia with an HMG-CoA reductase inhibitor (e.g. lovastatin, simvastatin and pravastatin) and aspirin, or a compound of formula I or Ia with an HMG-CoA reductase inhibitor and a beta adrenergic blocking drug.

Another example of combination therapy can be seen in treating obesity or obesity-related disorders, wherein the compounds of formula I or Ia may be effectively used in combination with for example, fenfluramine, dexfenfluramine, phentermine and $\beta_3$ adrenergic receptor agonist agents.

Still another example of combination therapy can be seen in treating diabetes and related disorders wherein the compounds of formula I or Ia can be effectively used in combination with for example sulfonylureas, biguanides, α-glucosidase inhibitors, other insulin secretogogues, insulin as well as the active agents discussed above for treating atherosclerosis.

In accordance with this invention, a pharmaceutically effective amount of a compound of formula I or Ia can be used for the preparation of a medicament useful for treating diabetes, treating obesity, lowering tryglyeride levels, raising the plasma level of high density lipoprotein, and for treating, preventing or reducing the risk of developing atherosclerosis, and for preventing or reducing the risk of having a first or subsequent atherosclerotic disease event in mammals, particularly in humans.

Additionally, an effective amount of a compound of formula I or Ia and a therapeutically effective amount of one or more active agents selected from the group consisting of: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozol; vitamin $B_6$ and the pharmaceutically acceptable salts thereof; vitamin $B_{12}$; an anti-oxidant vitamin; a beta-blocker; an angiotensin II antagonist; an angiotensin converting enzyme inhibitor; a platelet aggregation inhibitor; a fibrinogen receptor antagonist; aspirin; fenfluramine, dexfenfluramine, phentermine, $\beta_3$ adrenergic receptor agonists; sulfonylureas, biguanides, α-glucosidase inhibitors, other insulin secretogogues and insulin can be used together for the preparation of a medicament useful for the above-described treatments.

The tablets, capsules and the like may also contain a binder such as tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit is in the form of a capsule, it may also contain a liquid carrier, such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds of the present invention may also be administered parenterally, i.e, intramuscularly, intravenously, transdermally or subcutaneously. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Specific examples of formula I or Ia may require the use of protecting groups to enable their successful elaboration into the desired structure. Protecting groups may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Non-limiting examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Non-limiting examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

The process for making the compounds of the instant invention is generally depicted in Scheme 1 and 2 below:

SCHEME 1

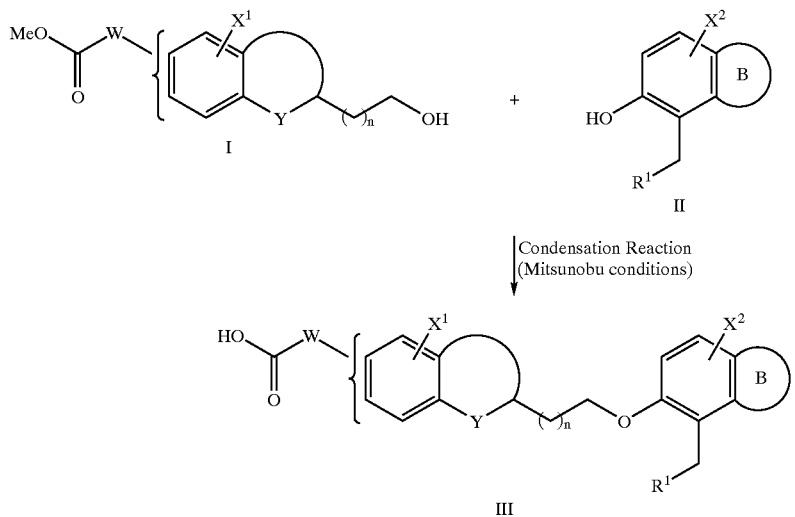

SCHEME 2

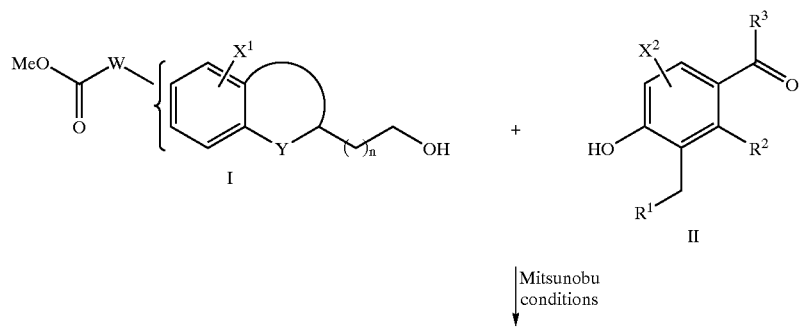

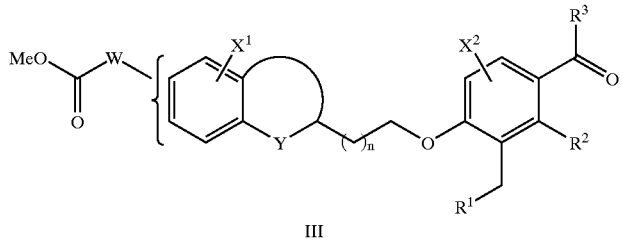

III

The invention is further illustrated in connection with the following non-limiting examples.

EXAMPLE 1

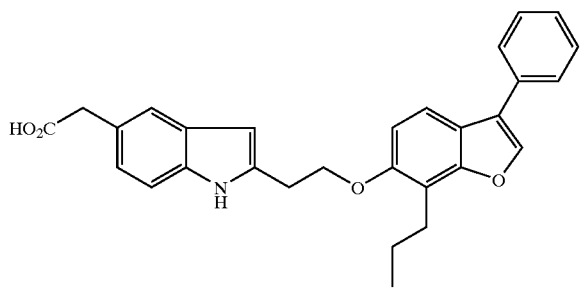

2-(2-(3-Phenyl-7-propylbenzofuran-6-yloxy)ethyl)indole-5-acetic Acid

Step A: Preparation of Methyl 4-amino-3-bromophenylacetate

To a suspension of 4-aminophenylacetic acid (7.4 g; 59.0 mmol) in ca. 90 ml of methanol, was added ca. 6.0 ml of concentrated sulfuric acid. After refluxing the brown solution for 2.5 hrs, it was concentrated to a dark oil. The oil was diluted with water and basified with 10 wt % $NaHCO_3$ to pH 9 and extracted with ethyl acetate. The organic layer was washed with water, brine and dried with $Na_2SO_4$. Evaporation in vacuo afforded 5.0 g of methyl 4-aminophenylacetate as a dark oil.

Without further purification the oil (5.0 g; 30.3 mmol) was diluted with 300 ml of THF. To this solution was added dropwise over 1 hour, a solution of pyridinium bromide perbromide (9.69 g; 30.3 mmol) in 300 ml of THF at room temperature. The light tan suspension was filtered and the filter cake was washed with ethyl acetate (2 times). The filtrate was treated with solid sodium bisulfite until the color faded, concentrated to an oil and diluted with ethyl acetate (ca. 200 ml). The organic layer was washed, dried ($Na_2SO_4$) and concentrated to a dark oil. The filter cake was dissolved in water, neutralized with 1 M sodium bicarbonate and extracted with ethyl acetate. The extracts were washed with water, dried ($Na_2SO_4$) and evaporated in vacuo to an oily residue, which was combined with the filtrate residue. Chromatography (silica gel, hexane:ethyl acetate::4:1) afforded 5.93 g of the title compound.

NMR ($CDCl_3$): δ7.34 (s,1H); 7.03 (d,1H); 6.72 (d,1H); 3.69 (s,3H); 3.50 (s, 2H)

Step B: Preparation of 1-(t-Butyldimethylsilyloxy)-3-butyne

To a solution of 3-butyne-1-ol (5.0 g; 71.3 mmol) in ca. 75 ml of methylene chloride was added tert-butyldimethylsilyl chloride (10.8 g; 71.6 mmol) and 7 ml of pyridine. The mixture was allowed to stir overnight at room temperature, diluted with methylene chloride, washed with water, 1M HCl, brine and dried ($Na_2SO_4$). Concentration in vacuo afforded the title compound as a colorless liquid.

NMR ($CDCl_3$): δ3.75 (t,2H); 2.41 (m,2H); 1.97 (s,1H); 0.91 (s,9H); 0.10 (s,6H)

Step C: Preparation of the Methyl 4-amino-3-(3-t-butyldimethylsilyloxy)-1-butynyl)phenylacetate Methyl 4-amino-3-(3-t-butyldimethylsilyloxy)-1-butynyl)phenylacetate (1.0 g, 4.1 mmol), 1-(t-butyldimethylsilyloxy)-3-butyne (840 mg, 4.55 mmol), dichlorobis(triphenylphosphine)-palladium(II) catalyst (57 mg, 2 mol %), copper(I) iodide (31 mg, 4 mol %) and ca. 10 ml of diethylamine were combined and heated at reflux overnight. The mixture was concentrated and purified by chromatography (silica gel, hexane:ethyl acetate 9:1 to 4:1) to afford 560 mg of the title compound as a dark liquid.

NMR ($CDCl_3$): δ7.17 (s,1H); 7.01 (d,1H); 6.66 (d, 1H); 3.85 (t,2H); 3.69 (s,3H); 3.48 (s,2H); 2.49 (t,2H); 0.91 (s,9H); 0.10 (s,6H)

Step D: Preparation of the Methyl 2-(2-(t-butyldimethylsilyloxyethyl)indole-5-acetate A mixture of methyl 4-amino-3-(3-t-butyldimethyl-silyloxy)-1-butynyl)phenylacetate (560 mg; 1.67 mmol), in acetonitrile (5 mL), and bis(acetonitrile) palladium(II) chloride (20 mg, ca. 5 mol %) were combined and heated under reflux for 30 minutes, concentrated and flash chromatographed (silica gel, hexane:ethyl acetate 9:1 to 4:1) to yield 417 mg of the title compound.

NMR ($CDCl_3$): δ7.45 (s,1H); 7.25 (d,1H); 7.19 (d,1H); 6.20 (s,1H); 3.94 (t,2H); 3.69 (s, 5H); 2.98 (t, 2H); 0.91 (s, 9H); 0.10 (s, 6H)

Step E: Preparation of the Methyl 2-(2-hydroxyethyl)indole-5-acetate

To a solution of methyl 2-(2-(t-butyldimethylsilyl-oxyethyl)-indole-5-acetate (400 mg; 1.15 mmol) in ca. 4 ml of THF was added a 1 M tetrabutylammonium fluoride in THF (1.2 mL; 1.05 eq) at 0° C. After 15 minutes, the reaction was allowed to warm to room temperature and stirred for an additional 3 hours. It was concentrated, diluted with water and extracted with ethyl acetate. The organic layer was washed with water, dried ($Na_2SO_4$), concentrated and chromatographed (silica gel, hexane:ethyl acetate 4:1) to yield 241 mg of the title compound as a colorless oil.

NMR ($CDCl_3$): δ7.45 (s,1H); 7.25 (d,1H); 7.19 (d,1H); 6.25 (s,1H); 3.80 (t,2H); 3.70 (s, 5H); 2.95 (t, 2H)

Step F: Preparation of Methyl 2-(2-(3-phenyl-7-propylbenzofuran-6-yloxy)-ethyl)-indole-5-acetate To a solution of the methyl 2-(2-hydroxyethyl)indole-5-acetate (37.6 mg; 0.16 mmol), $Ph_3P$ (47 mg; 1.1 eq), 3-phenyl-6-hydroxy-7-propylbenzofuran (45 mg; 1.1 eq) and THF (5 mL) was added diisopropyl azodicarboxylate (35 μL; 1.1 eq), and the mixture was stirred at room temperature overnight. The mixture was concentrated and chromatographed (silica gel, hexane:ethyl acetate::9:1 to 4:1) affording 18.6 mg of the title compound.

NMR ($CDCl_3$): δ7.77 (s,1H); 7.65 (d,1H); 7.40 (d,1H); 7.45 (d,1H); 6.93 (d,1H); 6.33 (s,1H); 4.37 (t,2H); 3.74 (s,2H); 3.70 (s, 3H); 3.32 (t,2H); 2.97 (t, 2H)

Step G: Preparation of 2-(2-(3-Phenyl-7-propylbenzofuran-6-yloxy)ethyl)indole-5-acetic Acid A solution of 18.6 mg (39.8 mmol) of methyl 2-(2-(3-phenyl-7-propylbenzofuran-6-yloxy)-ethyl)-indole-5-acetate in ca. 2.0 ml of methanol and 1 M aqueous LiOH (79.6 uL) was heated at 60° C. for 16 hours. The mixture was diluted with ethyl acetate and acidified to pH 5–6 with 1 M HCl, washed with water (2 times), brine (1 time) and dried over sodium sulfate and concentrated to afford 11.6 mg of the title compound. (mp=129–130° C.).

Mass Spec=471.3, calc=453.54+NH$_4$).

NMR (CDCl$_3$): δ7.77 (s,1H); 7.65 (d,1H); 7.40 (d,1H); 7.45 (d,1H); 6.93 (d,1H); 6.33 (s,1H); 4.37 (t,2H); 3.73 (s,2H); 3.30 (t,2H); 2.98 (t, 2H)

EXAMPLE 2

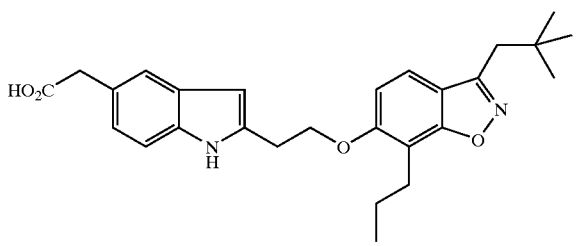

2-(2-(3-(2,2-Dimethylpropyl)-7-propylbenz[4,5]isoxazol-6-yloxy)ethyl)indole-5-acetic Acid Using the procedures in Example 1, steps F and G, the title compound was prepared from methyl 2-(2-hydroxyethyl)indole-5-acetate and 3-(2,2-dimethylpropyl)-7-propyl-6-hydroxybenz[4,5]isoxazole.

(dcp=110° C.; Mass Spec=449.4 (m+1), calc=448.6);

NMR (CDCl$_3$): δ8.35 (bs,1H); 7.40 (d,1H); 7.29 (m,1H); 7.07 (d,1H); 6.95 (d,1H); 6.33 (s,1H); 4.36 (t,2H); 3.73 (s,2H); 2.93 (t, 2H)

EXAMPLE 3

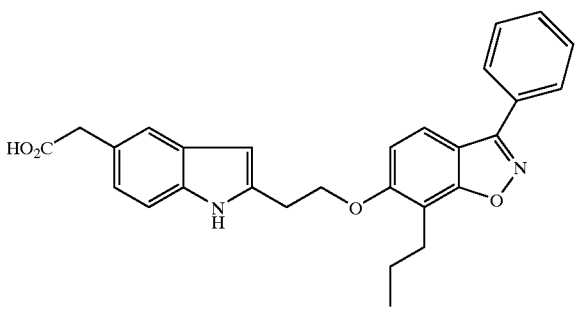

2-(2-(3-Phenyl-7-propylbenz[4,5]isoxazol-6-yloxy)ethyl)indole-5-acetic Acid

Using the procedures in Example 1, steps F and G, the title compound was prepared from methyl 2-(2-hydroxyethyl)indole-5-acetate and 3-phenyl-7-propyl-6-hydroxybenz[4,5]isoxazole as a colorless gum.

(Mass Spec=455 456(m+1), calc=453.5).

NMR (CDCl$_3$): δ7.95 (d,1H); 7.70 (d,1H); 7.55 (m,3H); 7.29 (d,2H); 7.10 (d,1H); 6.90 (d,1H); 6.33 (s,1H); 4.39 (t,2H); 3.70 (t,2H); 2.98 (t, 2H)

EXAMPLE 4

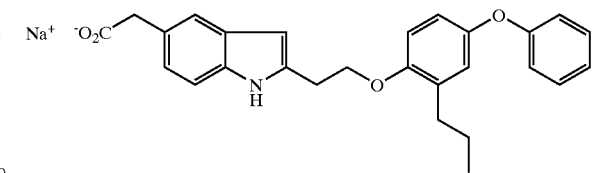

Step A: 4-Phenoxyphenyl Allyl Ether

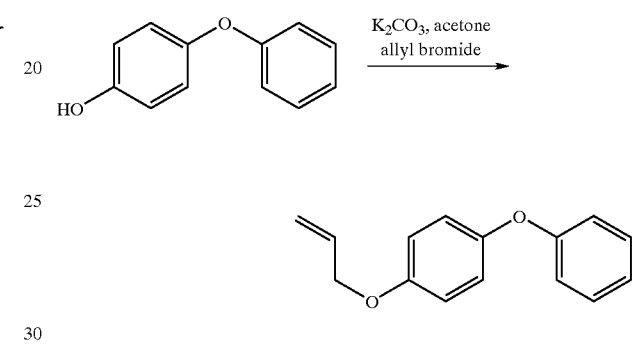

To a solution of the 4-phenoxyphenol (100 g, 0.54 mole) in acetone (500 mL) was added potassium carbonate (148 g, 1.07 mol) and allyl bromide (55.8 mL, 0.64 mole) and the resulting suspension heated to reflux. After 24 hours, the reaction was cooled to 0° C. and filtered. The filter cake was washed with ethyl acetate and the filtrate was concentrated to give a yellow oil which was partitioned between ethyl acetate (500 mL) and water (500 mL). The phases were separated and the organic washed with brine, dried and concentrated to give the allyl ether as a yellow oil (131 g).

Step B: 2-Allyl-4-phenoxyphenol

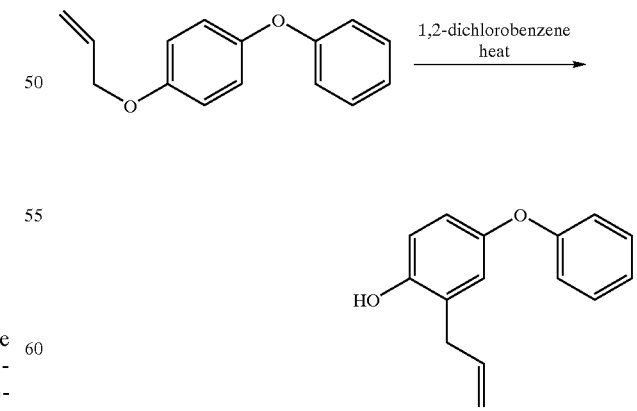

Claisen rearrangement: The allyl ether (131.6 g, 0.52 mole) was taken into 1,2-dichlorobenzene (600 mL) and the solution was heated to reflux. Approximatly 100 mL of distillate was removed to insure the complete removal of any residual ethyl acetate and the remaining solution left at reflux overnight. The reaction was then cooled and diluted with 3.5 liters of hexanes and 2N NaOH (1.8 liter) was added. The aqueous phase was removed and the organic extracted twice more with 900 mL portions of 2N NaOH. The combined aqueous solutions were then adjusted to pH~1 with 2N HCl and extracted with ether (1×2 liter). The ether extract was dried, filtered and concentrated to give an orange oil. (141.4 g).

Step C: 4-Phenoxy-2-propylphenol

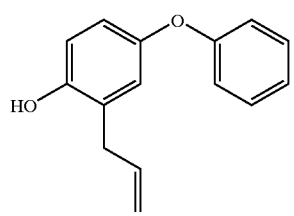

The phenol of Step B (141.4 g, 0.62 mole) was taken into 2 liters of ethyl acetate and the reaction vessel charged with 10% Pd/C catalyst (12 g). The reaction was stirred under $H_2$ until the starting material was consumed. The reaction mixture was filtered through Celite and the cake washed with ethyl acetate (total volume ~6 liters). The filtrate was concentrated to a dark oil which was taken into ether (1500 mL) and washed with 2N HCl (200 mL) sat'd. sodium bicarbonate and brine. The organic solution was dried over magnesium sulfate, filtered and concentrated to give a light brown oil. (125 g).

Step D: 2-(2-(4-Phenoxy-2-propylphenoxy)ethyl)indole-5-acetic Acid methyl Ester

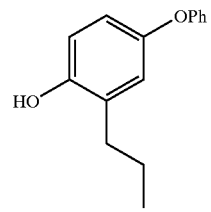

+

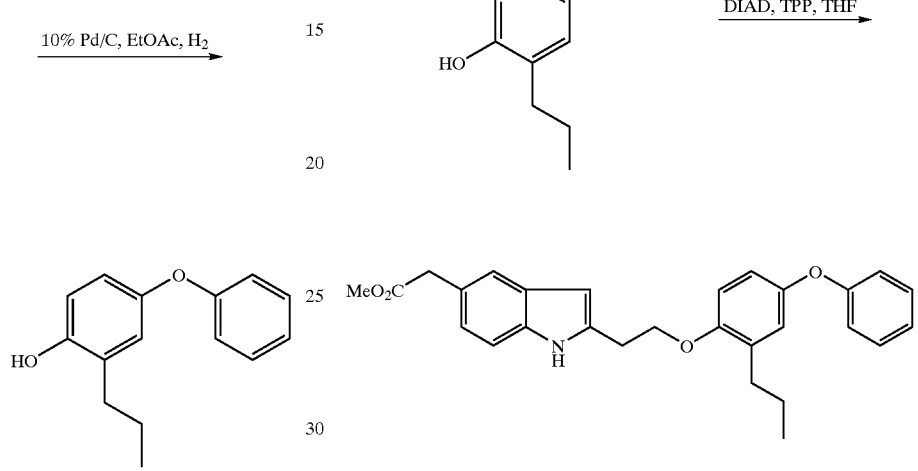

A solution of methyl 2-(2-hydroxyethyl)indole-5-acetate from Example 1, Step E (7.6 g), 4-phenoxy-2-propylphenol (8.28 g), triphenylphosphine (11.2 g), DIAD (8.5 mL) and THF (125 mL) was stirred under nitrogen at room temperature. After stirring overnight none of the starting indole remained as determined by TLC and the reaction was concentrated to a yellow oil. The oil was purified by silca gel chromatography (10%–20% ethyl acetate in hexanes) to give the desired product (9.0 g).

Step E: 2-(2-(4-Phenoxy-2-propylphenoxy)ethyl)indole-5-acetic Acid Sodium Salt

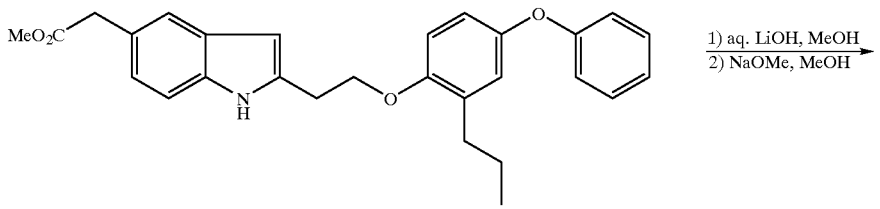

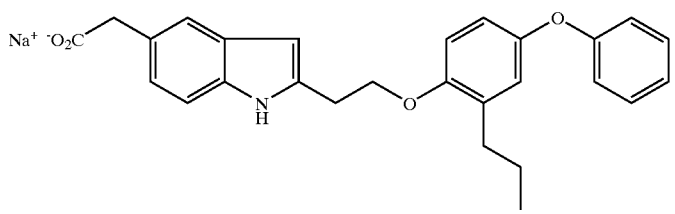

The ester (9.0 g) was taken into methanol (390 mL) and treated with 1M LiOH (51 mL) and the resulting solution was warmed to 60° C. After heating overnight there was no starting material remaining by TLC. The reaction was concentrated and the residue treated with 2N NaOH (26 mL) and then extracted with ethyl acetate (×2). The organic extracts were combined washed with water, brine dried and concentrated to give an off-white foam (8.9 g). This material was then taken into anhydrous methanol (170 mL) and treated with 0.5M NaOMe (41.4 mL). After stirring at room temperature for 20 min the reaction was concentrated to give a slightly yellow foam. (7.2 g).

Step F: Formation of the Crystalline Salt

The salt form of the compound can be protonated as shown in the following:

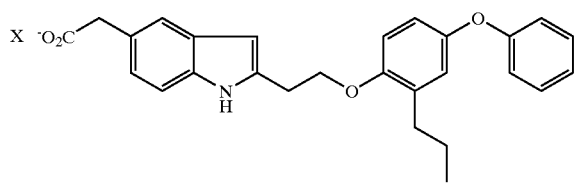

wherein X represents a positively charged counterion such as $Na^+$, $K^+$ and others known in the art. The salt forms can also be present in the form of a solvate.

In the case of $Na^+$, the sodium salt (5.23 g) was taken into 52.3 mL HPLC grade water and the solids dissolved upon heating to reflux. The dark brown solution was allowed to cool to 20° C. and then seeded. After 30 min visible solids are floating in the solution, after 1.25 there is a considerable amount of colorless solids present. After standing 18 hrs, the colorless solid is filtered from solution to give a crystalline compound pentahydrate.

(mp=86–87° C. Mass Spec=428.51.

NMR (CDCl$_3$):8.28 (s,1H); 7.41 (s,1H); 7.32–7.27 (m,3H); 7.18 (d,1H); 7.04 (t,1H); 6.99 (d,1H); 6.95 (d,1H); 6.89 (s,1H); 6.81 (dd, 1H); 6.77 (d, 1H); 6.27 (s, 1H); 4.19 (t, 2H); 3.61 (s, 1H); 3.21 (t, 2H); 2.63 (t,2H); 1.67–1.60 (m, 2H), 0.97 (t, 3H).

The pentahydrate above is but one crystal form. The compounds of the instant invention are intended to include all crystalline forms and are useful in various pharmaceutically acceptable salt forms, for the synthesis of antidiabetic compounds that are in turn useful for the treatment of the diseases disclosed herein in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug.

The crystalline forms of the compound are characterized below by virtue of their X-Ray Powder Diffraction (XRPD) patterns. The XRPD patterns are collected on a Philips APD 3720 automated powder diffractometer. The x-ray generator employs a copper target, an accelerating potential of 45 kV and a filament emission of 40 mA. Diffraction patterns are collected from 2° C. to 40° C.

The sodium salt of the compound (unsolvated material) was characterized as having an XRPD pattern at 5.5, 5.3, 4.9, 4.3, 4.1, 3.9, 3.8, 3.7, 3.6, 3.3, 3.2, 2.9, 2.6 and 2.3 angstroms. More complete XRPD data pertaining to the compound is shown below in Table 1.

TABLE 1

| Peak No. | Angle (deg) | Tip Width (deg) | Peak (cts) | Backg (cts) | D Spac (Ang) | I/I max (%) | Type A1 | A2 | Ot | Sign |
|---|---|---|---|---|---|---|---|---|---|---|
| 1 | 8.3325 | 0.48 | 10. | 6. | 10.6028 | 2.34 | x | x | | 0.83 |
| 2 | 9.7600 | 0.12 | 19. | 7. | 9.0550 | 4.43 | x | x | | 0.89 |
| 3 | 12.1375 | 0.36 | 10. | 8. | 7.2861 | 2.34 | x | x | | 1.05 |
| 4 | 14.1525 | 0.15 | 17. | 9. | 6.2529 | 3.85 | x | x | | 0.91 |
| 5 | 16.1575 | 0.15 | 46. | 12. | 5.4812 | 10.59 | x | x | | 2.09 |
| 6 | 16.6450 | 0.15 | 53. | 12. | 5.3218 | 12.20 | x | x | | 1.02 |
| 7 | 16.8200 | 0.15 | 41. | 12. | 5.2668 | 9.38 | x | x | | 0.91 |
| 8 | 17.6250 | 0.24 | 30. | 13. | 5.0280 | 6.93 | x | x | | 1.26 |
| 9 | 18.2600 | 0.07 | 154. | 13. | 4.8546 | 35.20 | x | x | | 1.38 |
| 10 | 18.9025 | 0.18 | 17. | 14. | 4.6910 | 3.85 | x | x | | 1.26 |
| 11 | 19.5625 | 0.12 | 34. | 14. | 4.5342 | 7.70 | x | x | | 0.76 |
| 12 | 20.5175 | 0.09 | 117. | 15. | 4.3252 | 26.70 | x | x | | 1.07 |
| 13 | 21.6225 | 0.21 | 48. | 16 | 4.1066 | 10.90 | x | x | | 2.88 |
| 14 | 22.6875 | 0.13 | 437. | 17 | 3.9162 | 100.00 | x | x | | 5.62 |
| 15 | 23.4200 | 0.09 | 128. | 18 | 3.7954 | 29.23 | x | x | | 0.78 |
| 16 | 23.8750 | 0.18 | 96. | 18 | 3.7241 | 21.99 | x | x | | 3.47 |
| 17 | 24.4900 | 0.12 | 72. | 18 | 3.6319 | 16.54 | x | x | | 3.02 |
| 18 | 25.0125 | 0.18 | 26. | 18 | 3.5572 | 5.95 | x | x | | 0.89 |
| 19 | 25.7275 | 0.18 | 20. | 19 | 3.4599 | 4.64 | x | x | | 0.83 |
| 20 | 26.6250 | 0.18 | 114. | 20 | 3.3453 | 26.21 | x | x | | 2.09 |
| 21 | 26.9725 | 0.09 | 246. | 20 | 3.3030 | 56.43 | x | x | | 1.74 |
| 22 | 27.9675 | 0.07 | 202. | 21 | 3.1877 | 46.16 | x | x | | 1.32 |
| 23 | 28.5925 | 0.24 | 30. | 22 | 3.1194 | 6.93 | x | x | | 1.05 |
| 24 | 30.8400 | 0.07 | 196. | 24 | 2.8970 | 44.87 | x | x | | 1.55 |
| 25 | 32.1275 | 0.18 | 38. | 24 | 2.7838 | 8.80 | x | x | | 1.82 |
| 26 | 32.6325 | 0.18 | 58. | 25 | 2.7419 | 13.22 | x | x | | 2.04 |
| 27 | 33.9250 | 0.18 | 174. | 26 | 2.6403 | 39.89 | x | x | | 5.13 |
| 28 | 35.1000 | 0.18 | 17. | 27 | 2.5546 | 3.85 | x | x | | 1.05 |
| 29 | 35.7950 | 0.24 | 32. | 27 | 2.5065 | 7.44 | x | x | | 3.16 |
| 30 | 36.8400 | 0.36 | 37. | 28 | 2.4378 | 8.52 | x | x | | 2.45 |
| 31 | 37.3975 | 0.15 | 35. | 28 | 2.4027 | 7.97 | x | x | | 1.07 |

TABLE 1-continued

| 32 | 37.8050 | 0.15 | 35. | 28 | 2.3778 | 7.97 | x | x | 1.15 |
| 33 | 38.5300 | 0.12 | 69. | 29 | 2.3347 | 15.77 | x | x | 1.15 |

Notes:
Generator settings: 45 kV, 40 mA
Cu alpha1, 2 wave lengths 1.54060, 1.54439 Ang
Step size, sample time 0.015 deg, 0.20 s, 0.075 deg/s
Monochromator used
Divergence slit Automatic (irradiated sample length 12.5 mm)
Peak angle range 2.007 – 40.002 deg
Range in D spacing 2.25207–43.9723 Ang
Peak position criterion Top of smoothed data
Cryst peak width range 0.00–2.00 deg
Minim peak significance 0.75
Number of peaks in file 33 (alpha1: 33, amorphous: 0)
Maximum intensity 437. cts, 2184.1 cps

EXAMPLE 5

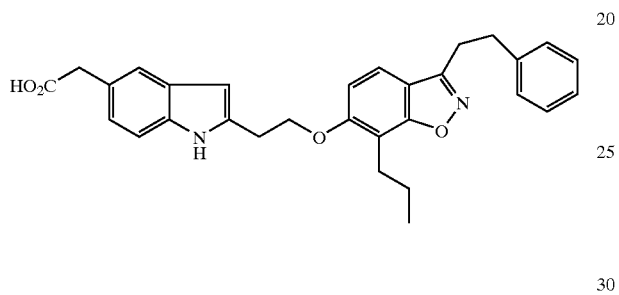

2-(2-(3-(2-Phenyl)ethyl-7-propylbenz[4,5]isoxazol-6-yloxy)ethyl)indole-5-acetic Acid Using the procedures in Example 1, steps F and G, the title compound was prepared from methyl 2-(2-hydroxyethyl)indole-5-acetate and 3-(2-phenyl)ethyl-7-(n-propyl)-6-hydroxybenz[4,5]isoxazole as a slightly tan solid.

EXAMPLE 6

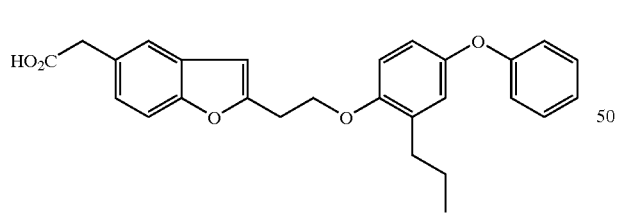

2-(2-(4-phenoxy-2-propylphenoxy)ethyl)benzofuran-5-acetic Acid

Using the procedure from Example 1, steps F and G, the title compound was prepared from methyl 2-(2-hydroxyethyl)benzofuran-5-acetate and 4-phenoxy-2-propylphenol as a colorless solid.

EXAMPLE 7

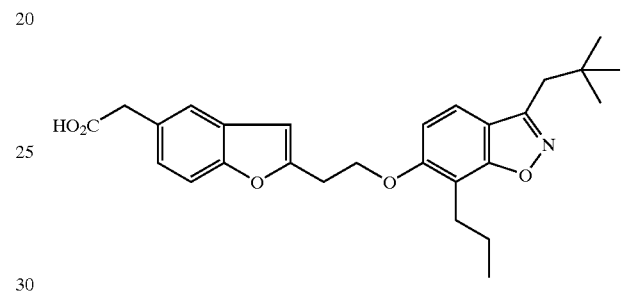

2-(2-(3-(2,2-Dimethylpropyl)-7-propylbenz[4,5]isoxazol-6-yloxy)ethyl)benzofuran-5-acetic Acid Using the procedure from Example 1, steps F and G, the title compound was prepared from methyl 2-(2-hydroxyethyl)benzofuran-5-acetate and 3-(2,2-dimethylpropyl)-7-propyl-6-hydroxybenz[4,5]isoxazole as a colorless oil.

EXAMPLE 8

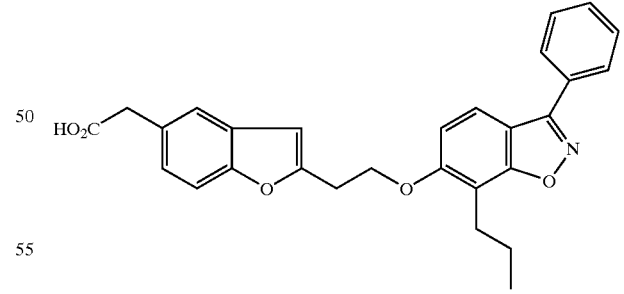

2-(2-(3-Phenyl-7-propylbenz[4,5]isoxazol-6-yloxy)ethyl)benzofuran-5-acetic Acid

Using the procedure from Example 1, steps F and G, the title compound was prepared from methyl 2-(2-hydroxyethyl)benzofuran-5-acetate and 3-phenyl-7-propyl-6-hydroxybenz[4,5]isoxazole as a colorless oil.

EXAMPLE 9

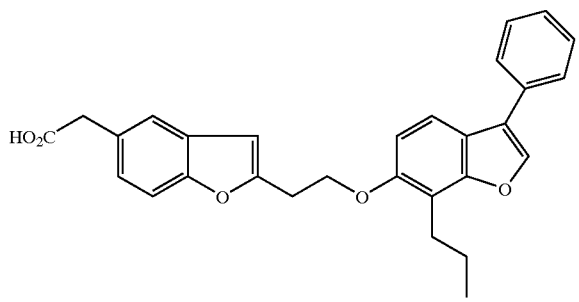

2-(2-(3-Phenyl-7-propylbenzofuran-6-yloxy)ethyl)-benzofuran-5-acetic Acid

Using the procedure from Example 1, steps F and G, the title compound was prepared from methyl 2-(2-hydroxyethyl)benzofuran-5-acetate and 3-phenyl-6-hydroxy-7-propylbenzofuran as a colorless oil.

EXAMPLE 10

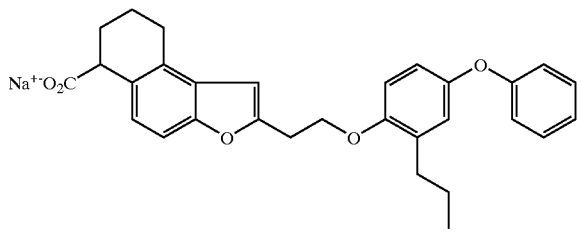

Step A

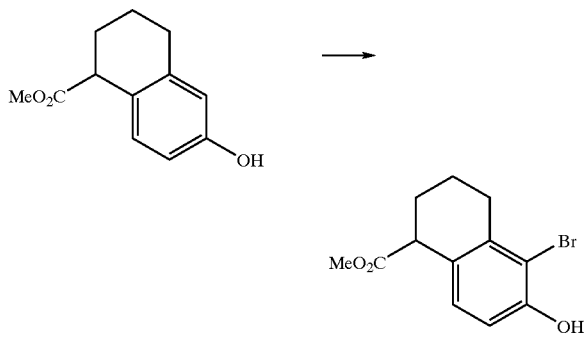

To a solution of methyl-6-hydroxy-1,2,3,4-tetrahydro-1-naphthoate (5 g) in THF (150 mL) was added dropwise over 1 hour a solution of pyridinium tribromide (7.8 g in 150 mL THF). After the addition was complete the reaction was stirred for an additional 30 minutes. The reaction was concentrated to remove most of the THF and the residue diluted with ethyl acetate and washed with water (×2), brine, dried over anhydrous sodium sulfate and concentrated to yield a colorless solid. This solid was recrystallized from toluene to give the desired monobromide.

Step B

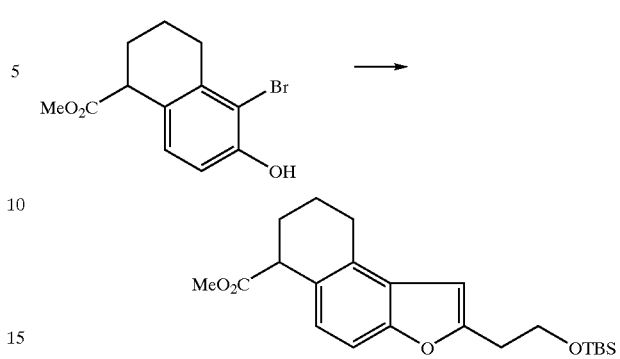

A suspension of the monobromide (4 g), copper oxide (3 g), and 4-t-butyltrimethylsiloxy-1-butyne (2.8 g) in pyridine (50 mL) was heated at reflux 18hrs, then cooled to room temperature. The reaction was filtered through a pad of Celite and the filtrate partitioned between ethyl acetate and water. The phases were separated and then the organic dried and concentrated to give a dark oil. The desired product was purified by silica gel chromatography to give 2.3 g of an amber oil.

Step C

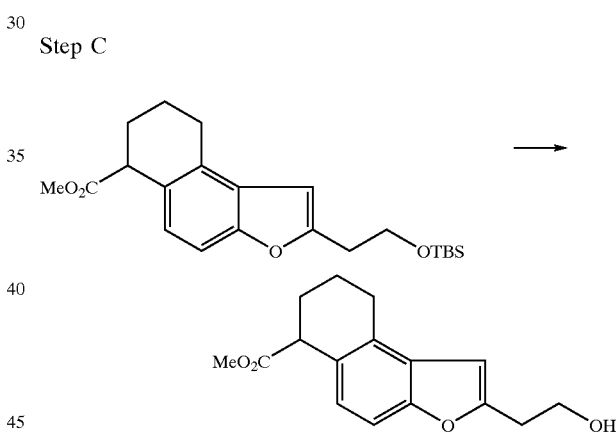

The TBS derivative (2.09 g) was dissolved in THF (10 mL) and chilled to 0° C. and treated with 1M HCl (6 mL). After stirring 4 hours the reaction was diluted with ethylacetate and washed with water, 1M sodium bicarbonate, water and brine. The solution was dried and concentrated to give an oil. The desired product was purified by silica gel chromatography to give an amber oil (1.3 g).

Step D

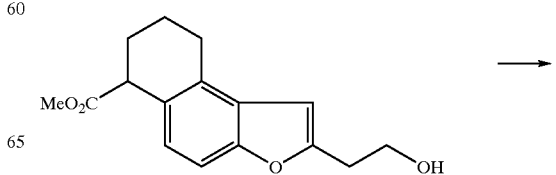

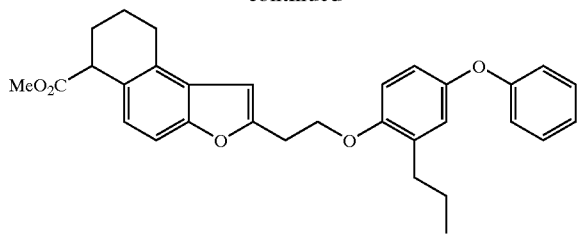

The alcohol (2.0 g), 2-propyl-4-phenoxyphenol (1.7 g), diisopropylazadicarboxylate (1.9 mL), triphenylphosphine (2.3 g) and THF (60 mL) were stirred at ambient temperature for 24 hrs then concentrated. The desired product was purified on silica gel chromatography to give cololess oil (1.2 g).

Step E

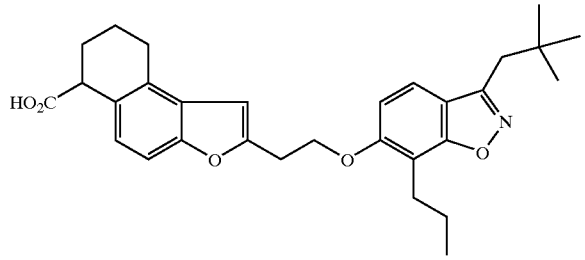

2-(2-(4-phenoxy-2-propylphenoxy)ethyl-4,5,6,7-tetrahydronaphtho[2,1-b]furan-7-carboxylic Acid Sodium Salt The ester (1.05 g) was taken into aq. dioxane (5 mL) and treated with 5N NaOH (1.3 mL) and the resulting solution warmed to 60° C. for 4 hrs. The reaction was acidified with 2N HCl and extracted with ethyl acetate. This solution was dried and concentrated. The residue was taken into dry methanol and treated with 0.5M sodium methoxide (1.0 eq) to give the desired compound as a sodium salt.

EXAMPLE 11

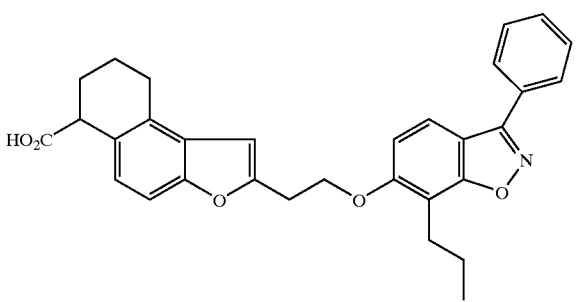

2-(2-(3-phenyl-7-propylbenz[4,5]isoxazol-6-yloxy)ethyl)-4,5,6,7-tetrahydronaphtho[2,1-b]furan-7-carboxylic Acid Using the procedure from Example 1, steps F and G, the title compound was prepared from methyl 2-(2-hydroxyethyl)-4,5,6,7-tetrahydronaphtho[2,1-b]furan-7-carboxylate and 3-phenyl-7-propyl-6-hydroxybenz[4,5]isoxazole as a colorless oil.

EXAMPLE 12

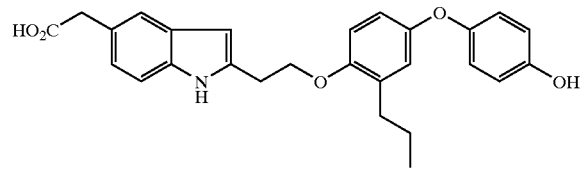

2-(2-(3-(2,2-dimethylpropyl)-7-propylbenz[4,5]isoxazol-6-yloxy)ethyl)-4,5,6,7-tetrahydronaphtho[2,1-b]furan-7-carboxylic Acid Using the procedure from Example 1, steps F and G, the title compound was prepared from methyl 2-(2-hydroxyethyl)-4,5,6,7-tetrahydronaphtho[2,1-b]furan-7-carboxylate and 3-(2,2-dimethylpropyl)-7-(n-propyl)-6-hydroxybenz[4,5]isoxazole as a colorless oil.

EXAMPLE 13

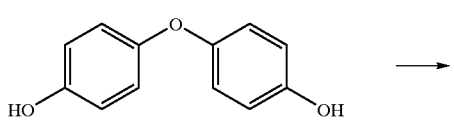

Step A: Preparation of 4-(4-hydroxy)phenoxyphenylbenzoate

To a solution of 4,4'-oxydiphenol (2 g, 10 mmoL), pyridine (2.5 mL), and dichloromethane (35 mL) was added benzoyl chloride (1.2 mL) and the resulting solution was stirred overnight at ambient temperature. The reaction was diluted with dichloromethane washed with water, 1M HCl, brine and dried over anhydrous sodium sulfate. After removal of solvent the desired produced was purified by silica gel chromatography (hexanes:ethyl acetate 7:3) to give a colorless oil. (2.26 g).

Step B: Preparation of 4-(3-propyl-4-hydroxy)phenoxyphenylbenzoate

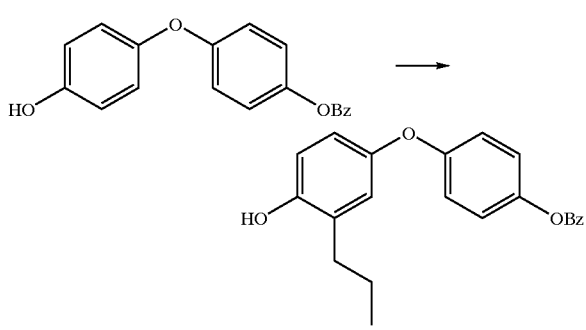

Using the procedures from Example 4, steps A through C, the title compound was prepared from 4-(4-hydroxy)phenoxyphenylbenzoate.

Step C: Preparation of 2-(2-(4-(4-benzoyloxy)phenoxy-2-propylphenoxy)ethyl)indole-5-acetic Acid Methyl Ester

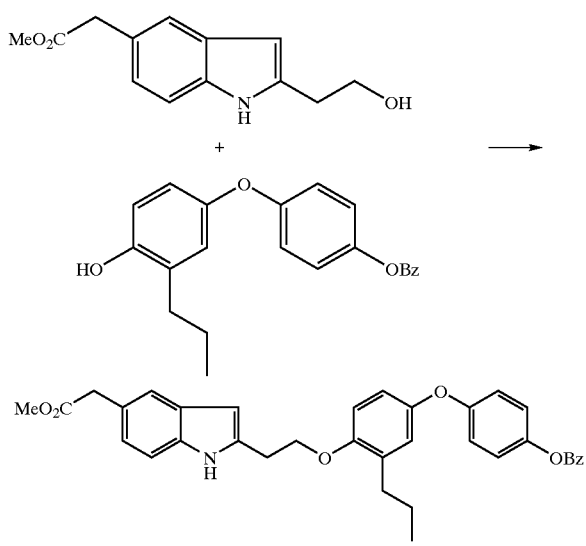

Using the procedure from Example 1, step F, the title compound was prepared from 2-(2-hydroxyethyl)indole-5-acetic Acid methyl ester and 4-(3-propyl-4-hydroxy)phenoxyphenylbenzoate.

Step D: Preparation of 2-(2-(4-(4-hydroxy)phenoxy-2-propylphenoxy)ethyl)indole-5-acetic Acid Methyl Ester

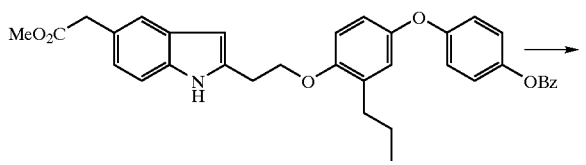

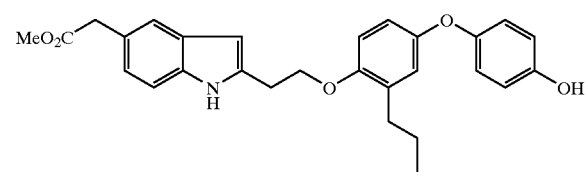

A solution of methanol (12 mL), water (6 mL), triethylamine (6 mL) and 2-(2-(4-(4-benzoyloxy)phenoxy-2-propylphenoxy)ethyl)indole-5-acetic acid methyl ester (760 mg) was warmed to reflux for 3 hours. The reaction was cooled and concentrated. The residue was taken into ethyl acetate and washed with water, brine and dried over anhydrous sodium sulfate to give an amber oil. The desired compound was obtained by silica gel chromatography (hexanes:ethyl acetate) as a slightly amber colored oil (535 mg).

Step E: Preparation of 2-(2-(4-(4-hydroxy)phenoxy-2-propylphenoxy)ethyl)indole-5-acetic Acid

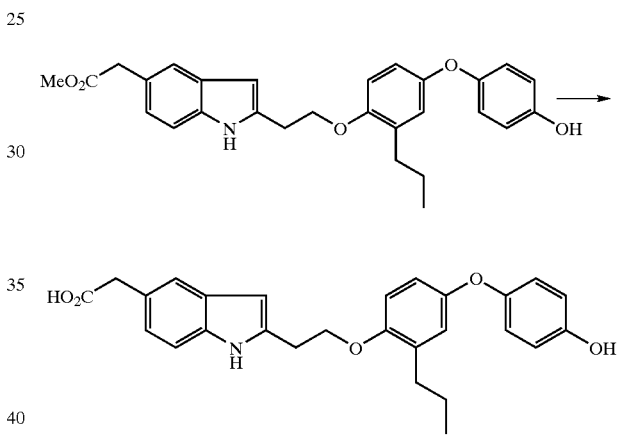

A solution of 2-(2-(4-(4-hydroxy)phenoxy-2-propylphenoxy)ethyl)indole-5-acetic acid methyl ester (23 mg), dioxane (1 mL) and 5N NaOH (50 μL) was heated at 60° C. for 1 hour. The solution was cooled and acidified with 2N HCl and extracted with ethyl acetate. The organic solution was dried over anhydrous sodium sulfate and concentrated to yield the desired product as a brown oil (18 mg).

$^1$HNMR (500 mHz, $CD_3CN$) 7.33 (s,1H), 4.23 (t,3H), 3.62 (s,2H), 3.19 (t,2H), 2.45 (t,2H), 1.46–1.39 (m,2H), 0.90 (t,3H)

EXAMPLE 14

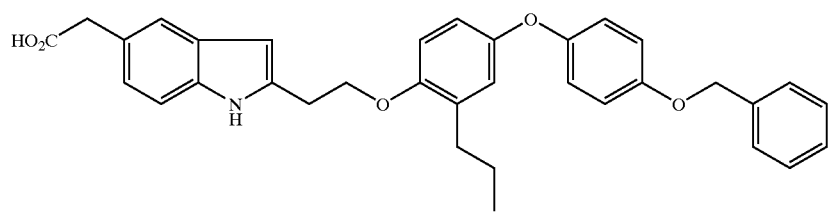

Step A: Preparation of Methyl 2-(2-(4-(4-benzyloxy) phenoxy-2-propylphenoxy)ethyl)indole-5-acetate To a solution of methyl 2-(2-(4-(4-hydroxy)phenoxy-2-propylphenoxy)ethyl)indole-5-acetate, Example 13, Step D, (21 mg) in DMF (1 mL) was added sodium hydride (2 mg, 60% in oil) and the reaction was stirred for 30 minutes. Benzyl bromide (5.5 μL) was then added and the reaction was stirred for 12 hours at room temperature. Water was added and the reaction extracted with ethyl acetate, dried and concentrated. The desired compound was purified by silica gel chromatography (hexanes:ethyl acetate 70:30) (17.4 mg).

Step B: Preparation of 2-(2-(4-(4-benzyloxy)phenoxy-2-propylphenoxy)ethyl)indole-5-acetic Acid A solution of methyl 2-(2-(4-(4-benzyloxy)phenoxy-2-propylphenoxy)ethyl)indole-5-acetate (17 mg), dioxane (1 mL) and 5N NaOH (31 μL) was warmed to 60° C. for 12 hours. The reaction was cooled and acidified with 1M HCl and the product extracted with ethyl acetate to yield 8.8 mg.

$^1$HNMR (500 mHz, CDCl$_3$) 6.30 (s,1H), 5.05 (s,2H), 4.21 (t,3H), 3.74 (s,2H), 3.25 (t,2H), 0.96 (t,3H).

EXAMPLE 15

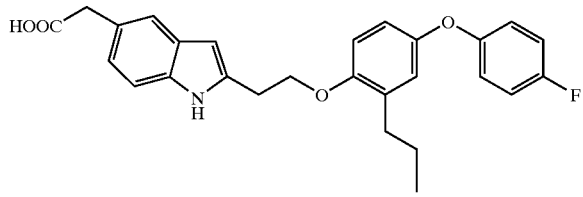

2-(2-(4-(4-Fluorophenoxy)-2-propylphenoxy)ethyl) indole-5-acetic Acid

Step A: Preparation of 4-(4-fluorophenoxy)benzaldehyde

A solution of 4-fluorophenol (4.52 g, 40.29 mmol), 4-fluorobenzaldehyde (5.00 g, 40.29 mmol) and potassium carbonate (6.70 g, 48.35 mmol) in DMAC (40 mL) was refluxed for 12 h and cooled to room temperature. Water was added and the reaction mixture was extracted with ethyl acetate. The organic extract was washed with brine, dried over sodium sulfate, filtered and concentrated to afford an oil which was chromatographed on silica gel (15% ethyl acetate/hexane) to afford the title compound.

Step B: Preparation of 4-(4-fluorophenoxy)phenol

A solution of 4-(4-fluorophenoxy)benzaldehyde (9.00 g, 41.63 mmol) in CHCl$_3$ (75 mL) was treated with m-chloroperbenzoic acid (46–85%, 15.80 g, 52.00 mmol) and stirred for 3 h at room temperature. The reaction was washed with sat. aq. NaHSO$_3$, sat. aq. NaHCO$_3$, and water. The organic layer is concentrated and the residual oil taken up in MeOH (10 mL) containing a few drops of conc. HCL and stirred for 1 h at room temperature. The solvent is removed in vacuo and the resulting oil was chromatographed on silica gel (20% ethyl acetate/hexane) to afford the title compound.

Step C: Preparation of 4-(4-fluorophenoxy)phenyl Allyl Ether

A solution of 4-(4-fluorophenoxy)phenol (4.75 g, 23.30 mmol), potassium carbonate (4.17 g,. 30.30 mmol) and allyl bromide (2.22 mL, 25.60 mmol) in DMF (50 mL) was stirred for 5 h at 60° C. After cooling, the reaction mixture was neutralized with 1 N HCL and extracted with ethyl acetate. The organic extract was washed with brine, dried over sodium sulfate, filtered and concentrated to afford an oil which was chromatographed on silica gel (15% ethyl acetate/hexane) to afford the title compound.

Step D: Preparation of 4-(4-fluorophenoxy)-2-allylphenol 4-(4-fluorophenoxy)phenyl allyl ether (4.00 g, 16.37 mmol) was taken up in 1,2-dichlorobenzene (50 mL) and refluxed for 48 h. After cooling, the solvent was removed in vacuo and the resulting crude oil was chromatographed on silica gel (15% ethyl acetate/hexane) to afford the title compound.

Step E: Preparation of 4-(4-fluorophenoxy)-2-propylphenol

A solution of 4-(4-fluorophenoxy)-2-allylphenol (2.30 g, 9.42 mmol) and 5% Pd/C (0.90 g) in ethyl acetate (30 mL) was stirred under H$_2$ atmosphere for 3 h at room temperature. The reaction mixture was filtered through a short pad of silica gel and concentrated in vacuo to afford the title compound which was used as is.

Step F: Preparation of 2-(2-(4-(4-fluorophenoxy)-2-propylphenoxy)ethyl)-indole-5-acetate A solution of 4-(4-fluorophenoxy)-2-propylphenol (0.17 g, 0.70 mmol), 2-(2-hydroxyethyl)indole-5-acetate (0.15 g,. 0.64 mmol) and triphenylphosphine (0.18 g, 0.67 mmol) in THF (3 mL) was treated with diisopropylazodicarboxylate (0.13 mL, 0.67 mmol) and stirred 16 h at room temperature. The reaction mixture was concentrated and chromatographed on silica gel (15% ethyl acetate/hexane) to afford the title compound.

Step G: Preparation of 2-(2-(4-(4-fluorophenoxy)-2-propylphenoxy)-ethyl)-indole-5-acetic Acid A solution of 2-(2-(4-(4-fluorophenoxy)-2-propylphenoxy)-ethyl)-indole-5-acetate (mg, mmol) in MeOH (mL) and LiOH (mL) was heated at reflux for 3 hours. The mixture was acidified to pH 6 with 1 N HCL and extracted with ethyl acetate. The organic layer was dried over sodium sulfate, filtered and concentrated to afford the title compound.

$^1$NMR (CDCl$_3$, ppm) δ8.38 (broad s, 1H), 7.46 (s, 1H), 7.25 (d, 1H),6.75–7.10 (m, 7H), 6.30 (s, 1H), 4.23 (t, 2H), 3.73 (s, 2H), 3.27 (t, 2H), 2.64 (t, 2H), 1.65 (m, 2H), 0.98 (t, 3H)

EXAMPLE 16

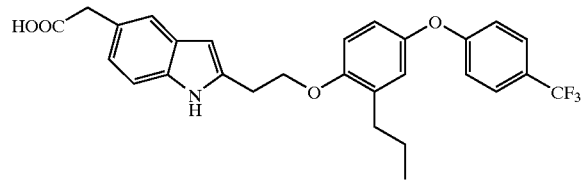

2-(2-(4-(4-Trifluoromethylphenoxy)-2-propylphenox=)-ethyl)indole-5-acetic Acid

Step A: Preparation of 4-(4-trifluoromethylphenoxy)-2-propylphenol

Using the procedures in Example 15, steps A through E, and substituting 4-trifluoromethylphenol for 4-fluorophenol in step A, the title compound was prepared.

Step B: Preparation of 2-(2-(4-(4-trifluoromethylphenoxy)-2-propylphenoxy)ethyl)indole-5-acetic Acid Using the procedures in Example 15, steps F and G, the title compound was prepared from methyl 2-(2-hydroxyethyl)indole-5-acetate and 4-(4-trifluoromethylphenoxy)-2-propylphenol.

$^1$NMR (CDCl$_3$, ppm) δ8.39 (broad s, 1H), 7.46 (s, 1H), 7.22–7.43 (m, 2H), 7.06 (d, 2H), 6.93 (d, 2H), 6.89 (s, 1H), 6.81 (s, 1H), 6.30 (s, 1H), 4.23 (t, 2H), 3.73 (s, 2H), 3.25 (t, 2H), 2.63 (t, 2H), 1.65 (m, 2H), 0.99 (t, 3H)

EXAMPLE 17

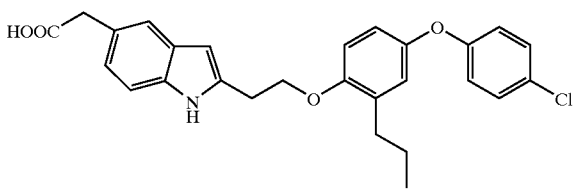

2-(2-(4-(4-Chlorophenoxy)-2-propylphenoxy)ethyl)indole-5-acetic Acid

Step A: Preparation of 4-(4-chlorophenoxy)-2-propylphenol

Using the procedures in Example 15, steps A through E, and substituting 4-chlorophenol for 4-fluorophenol in step A, the title compound was prepared.

Step B: 2-(2-(4-(4-Chlorophenoxy)-2-propylphenoxy)ethyl)indole-5-acetic Acid

Using the procedures in Example 15, steps F and G, the title compound was prepared from methyl 2-(2-hydroxyethyl)indole-5-acetate and 4-(4-chlorophenoxy)-2-propylphenol.

$^1$NMR (CDCl$_3$, ppm) δ8.37(broad s, 1H), 7.46 (s, 1H), 7.20–7.28 (m, 2H), 7.06 (d, 1H), 6.80–6.88 (m, 5H), 6.30 (s, 1H), 4.23 (t, 2H), 3.73 (s, 2H), 3.26 (t, 2H), 2.63 (t, 2H), 1.65 (m, 2H), 0.99 (t, 3H)

EXAMPLE 18

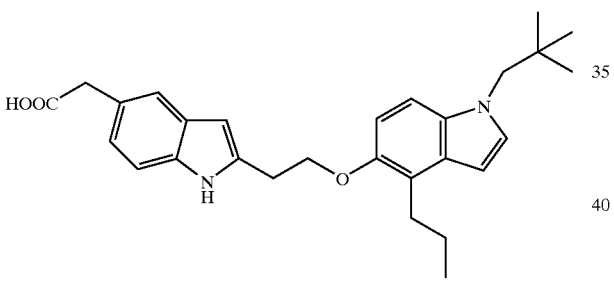

2-(2-(5-(4-Propyl-N-neopentyl)indolyloxy)ethyl)indole-5-acetic Acid

Step A: Preparation of 5-allyloxyindole

5-Hydroxyindole (1.00 g, 7.29 mmol) and potassium carbonate (1.38 g, 9.94 mmol) were taken up in 20 mL of dimethylformamide (DMF) and stirred at 60° C. for 0.5 hours. Allyl bromide (0.57 mL, 6.62 mmol) was added and the reaction was stirred for an additional 18 hours then cooled and diluted with ethyl acetate. The organic layer was washed with water, brine, dried over magnesium sulfate, filtered, concentrated in vacuo, and the crude residue was purified by flash chromatography on silica gel (10% ethyl acetate/hexane) to provide the title compound.

Step B: Preparation of 5-allyloxy-N-neopentylindole

To a solution of sodium hydride (60%, 254 mg, 6.35 mmol) in 15 mL tetrahydrofuran (THF) was added 5-allyloxyindole (Step A; 1.0 g, 5.77 mmol) in 5 mL THF and the mixture was stirred for 1 hour at ambient temperature. Neopentyl iodide (0.69 mL, 6.35 mmol) was added and the reaction heated to reflux for 21 hours. After cooling, the reaction was quenched with saturated aqueous ammonium chloride and extracted with ethyl acetate. The organic layer was washed with water, brine, dried over magnesium sulfate, filtered, concentrated in vacuo, and the crude residue purified by flash chromatography on silica gel (15% ethyl acetate/hexane) to provide the title compound.

Step C: Preparation of 4-allyl-5-hydroxy-N-neopentylindole

5-Allyloxy-N-neopentylindole (Step B; 1.4 g, 4.93 mmol) was refluxed in 20 mL 1,2-dichlorobenzene for 4 hours. The reaction mixture was cooled and immediately purified by flash chromatography on silica gel (gradient elution: hexane then 10% ethyl acetate/hexane) to provide the title compound.

Step D: Preparation of 5-hydroxy-4-propyl-N-neopentylindole

4-Allyl-5-hydroxy-N-neopentylindole (Step C; 1.0 g, 3.54 mmol) was taken up in 25 mL ethyl acetate and hydrogenated (1 atm) at ambient temperature using 5% palladium on charcoal (40 mg) for 2 hours. The reaction was filtered through celite and concentrated in vacuo to provide the title compound which was used without further purification.

Step E: Preparation of 2-(2-(5-(4-propyl-N-neopentyl)indolyloxy)ethyl)indole-5-acetic Acid Using the procedures in Example 15, steps E and F, the title compound was prepared from 5-hydroxy-4-propyl-N-neopentylindole and 2-(2-hydroxyethyl)indole-5-acetate.

$^1$NMR (CDCl$_3$, ppm) 8.68 (broad s, 1H), 7.45 (s, 1H), 7.24 (d, 1H), 7.00–7.14 (m, 2H), 6.88 (d, 1H), 6.45 (d, 1H), 6.29 (s, 1H), 4.27 (t, 2H), 3.83 (s, 2H), 3.71 (s, 2H), 3.25 (t, 2H), 2.90 (t, 2H), 1.73 (m, 2H), 1.02 (t, 3H), 1.00 (s, 9H)

EXAMPLE 19

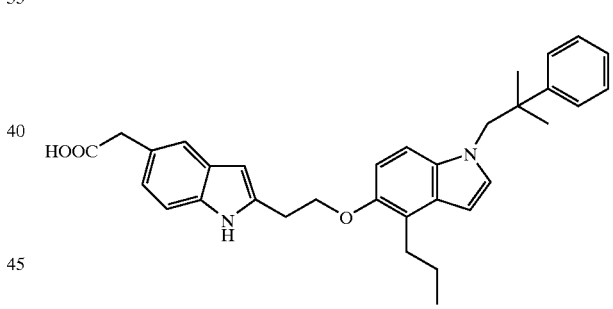

2-(2-(5-(4-propyl-N-neophyl-indolyloxy)ethyl)-indole-5-acetic Acid

Step A: Preparation of 5-hydroxy-4-propyl-N-neophylindole

Using the Procedures in Example 18, steps A through E, and substituting neophyl chloride for neopentyl iodide in step B, the title compound was prepared.

Step B: Preparation of 2-(2-(5-(4-propyl-N-neophyl)indolyloxy)ethyl)-indole-5-acetic Acid Using the procedures in Example 15, steps E and F, the title compound was prepared from 5-hydroxy-4-propyl-N-neophyllindole and 2-(2-hydroxyethyl)indole-5-acetate.

$^1$NMR (CDCl$_3$, ppm) δ8.65 (broad s, 1H), 7.46 (s, 1H), 7.33 (d, 2H), 7.05 (dd, 1H), 6.95 (dd, 1H), 6.81 (dd, 1H), 6.52 (d, 1H), 6.30 (dd, 2H), 4.27 (t, 2H), 4.17 (s, 2H), 3.70 (s, 2H), 3.23 (t, 2H), 2.88 (t, 2H), 1.22 (m, 2H), 1.40 (s, 6H), 0.98 (t, 3H)

EXAMPLE 20

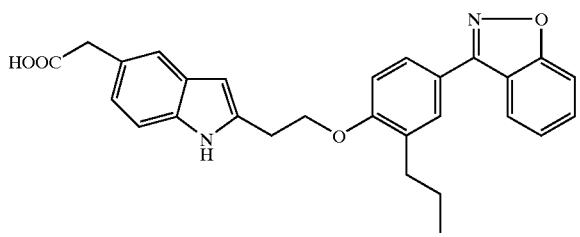

2-(2-((4-Benz[4,5]isoxazol-3-yl)-2-propylphenoxy)ethyl)indole-5-acetic Acid

Step A: Preparation of 4-hydroxy-5-propyl-2'-fluorobenzophenone

A 0° C. suspension of 2-fluorobenzoyl chloride (1.3 mL, 11.03 mmol) in 15 mL of 1,2-dichloroethane was treated with aluminum chloride (1.0 g, 7.35 mmol). The suspension was vigorously stirred for 15 minutes. A solution of 2-propylphenol (1.0 g, 7.35 mmol) in 5 mL of 1,2-dichloroethane was added dropwise. The mixture was allowed to stir and gradually warm to 25° C. over 6 hours. The mixture was slowly added to a stirred mixture of water and methylene chloride. The organic phase was dried over magnesium sulfate, filtered and concentrated to a solid. The crude residue was purified via flash chromatography on silica gel (15% ethyl acetate/hexane eluent) to afforded the title compound.

Step B: Preparation of 4-hydroxy-5-propyl-2'-fluorobenzophenone Oxime

A solution of 4-hydroxy-5-propyl-2'-fluorobenzophenone (Step A; 1.35 g, 5.23 mmol) in 15 mL of pyridine was treated with hydroxylamine hydrochloride (1.82 g, 26.15 mmol). The mixture was refluxed for 24 hours, cooled and the pyridine removed in vacuo. The residue was taken up in ethyl acetate and washed with 1N hydrochloric acid, water, brine, dried over MgSO$_4$, filtered and concentrated in vacuo. The crude residue was purified via flash chromatography on silica gel (20% ethyl acetate/hexane eluent) to yield the title compound.

$^1$NMR (CDCl$_3$, ppm) δ0.96 (t, 3H), 1.22 (m, 2H), 1.56 (t, 2H), 6.82 (d, 1H), 7.13–7.57 (m, 7H); ESI: MS m/e=259 (M+1)

Step C: Preparation of 4-(1,2-benz[4,5]isoxazol-3-yl)-2-propylphenol

Sodium hydride (60%; 160 mg, 4.0 mmol) was taken up in 7 mL of dimethylformamide (DMF) and 7 mL of benzene. 4-hydroxy-5-propyl-2'-fluorobenzophenone oxime (Step B; 517 mg, 2.0 mmol) was added in 3 mL of DMF and 3 mL of benzene and the reaction stirred at 50° C. for 2 hours. After cooling, the reaction was quenched with saturated aqueous ammonium chloride and extracted with ethyl acetate. The organic phase was washed with water, brine, dried (MgSO$_4$), filtered and concentrated in vacuo. The crude residue was purified by flash chromatography on silica gel (10% ethyl acetate/hexane eluent) to afford the title compound.

Step D: Preparation of 2-(2-((4-benz[4,5]isoxazol-3-yl)-2-propylphenoxy)ethyl)-indole-5-acetic Acid Using the procedures in Example 15, steps E and F, the title compound was prepared from 4-(1,2-benzisoxazol-3-yl)-2-propylphenol and 2-(2-hydroxyethyl)indole-5-acetate.

$^1$NMR (CDCl$_3$, ppm) δ8.32 (broad s, 1H), 7.92 (d, 1H), 7.76–7.81 (m, 2H), 7.55–7.65 (m, 2H), 7.46 (s, 1H), 7.35–7.41 (td, 1H), 7.07 (d, 1H), 7.02 (d, 1H) 6.33 (s, 1H), 4.36 (t, 2H), 3.72 (s, 2H), 3.68 (s, 3H), 3.31 (t, 2H), 2.75 (t, 2H), 1.22 (m, 2H), 1.03 (t, 3H)

BIOLOGICAL ASSAYS

I. White Adipose Tissue in vitro Assay

The ability of compounds of the present invention to enhance the insulin activation of $^{14}$C-glucose incorporation into glycogen in white adipose tissue (WAT) was determined by the following assay.

This assay measures the efficacy of the instant compounds to enhance the insulin activation of $^{14}$C-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 μg/ml streptomycin sulfate, 0.25 μg/ml amphotericin B), hereafter called culture medium. Epididymol fat pads are minced with scissors into small fragments, approximately 1 mm in diameter. Minced WAT fragments (100 mg) are incubated in a total volume of 0.9 ml culture medium containing 1 mU/ml insulin and test compound in tissue culture incubator at 37° C. with 5% $CO_2$ with orbital shaking for 3 hours. $^{14}$C-labeled glucose is added and incubation continued for 2 hours. Tubes are centrifuged at low speed, infranatant is removed and 1 M NaOH is added. Incubation of alkali-treated WAT for 10 minutes at 60° C. solubilizes tissue. Resulting tissue hydrolyzate is applied to Whatman filter paper strips which are then rinsed in 66% ethanol followed by 100% acetone which removes unincorporated $^{14}$C-glucose from bound $^{14}$C-glycogen. The dried paper is then incubated in solution of amyloglucosidase to cleave glycogen into glucose. Scintillation fluid is added and samples are counted for $^{14}$C activity. Test compounds that resulted in $^{14}$C activity substantially above incubations with insulin alone are considered active insulin-enhancing agents. Active compounds were titrated to determine the compound concentration which resulted in 50% of maximum enhancement of insulin activation and were termed EC$_{50}$ values. EC$_{50}$ values for the instant compounds were found to be 50 μM or less, preferably 5.0 to 0.0001 μM or less.

II. PPAR Receptor Binding Assay

Compounds of the instant invention which are useful for the above discussed treatments can be identified and/or characterized by employing the PPAR δ, and γ binding assays. The assays are useful in predicting or quantitating in vivo effects having to do with the control or modulation of glucose, free fatty acid, triglyceride, insulin or cholesterol. To evaluate IC$_{50}$ or EC$_{50}$, values the compounds were titrated in the appropriate assay using different concentrations of the compound to be tested. To obtain the appropriate values (%Inhibition-IC$_{50}$, or %Activation-EC$_{50}$), the data resulting from the assays were then analyzed by determining the best fit of a 4 parameter function to the data using the Levenberg-Marquardt non-linear fitting algorithm in Kaleidagraph (Synergy Software, Reading, Pa.). The human nuclear receptor cDNA for PPARδ (hPPARδ) has been cloned from a human osteosarcoma cell cDNA library and is fully described in A. Schmidt et al., Molecular Endocrinology, 6:1634–1641 (1992), herein incorporated by reference in its entirety. See A. Elbrecht et al., Biochem. and Biophy. Res. Comm. 224:431–437 (1996) and T. Sher et al., Biochem. 32:5598–5604 (1993) for a description of the human nuclear receptor gene PPARγ and α.

The hPPARδ binding assay comprises the steps of:
(a) preparing multiple test samples by incubating separate aliquots of the receptor hPPARδ with a test compound in TEGM containing 5–10% COS-1 cell cytoplasmic lysate and 2.5 nM labeled ([$^3$H$_2$]Compound D, 17 Ci/mmole) for a minimum of 12 hours, and preferably for about 16 hours, at 4° C., wherein the concentration of the test compound in each test sample is different, and preparing a control sample by incubating a further separate aliquot of the receptor hPPARδ under the same conditions but without the test compound; then (b) removing unbound ligand by adding dextran/gelatin-coated charcoal to each sample while maintaining the samples at 4° C. and allowing at least 10 minutes to pass, then (c) subjecting each of the test samples and the control sample from step (b) to centrifugation at 4° C. until the charcoal is pelleted; then (d) counting a portion of the supernatant fraction of each of the test samples and the control sample from step (c) in a liquid scintillation counter and analyzing the results to determine the $IC_{50}$ of the test compound.

In the hPPARδ binding assay, preferably at least four test samples of varying concentrations of a single test compound are prepared in order to determine the $IC_{50}$.

Particular terms and abbreviations used herein are defined as follows: gst is glutathione-S-transferase; EDTA is ethylenediamine-tetraacetic acid; HEPES is N-[2-hydroxyethyl]-piperazine-N'-[2-ethanesulfonic acid]; FCS is fetal calf serum; Lipofectamine is a 3:1 (w/w) liposome formulation of the polycationic lipid 2,3-dioleyloxy-N-[2(spermine-carboxamido)ethyl]-N,N-dimethyl-1-propanaminium-trifluoroacetate and the neutral lipid dioleoyl phosphatidylethanolamine in water; G418 is geneticin; MEM is Minimum Essential Medium; Opti MEM 1 Reduced-Serum Medium is an aqueous composition containing HEPES buffer, 2400 mg/L sodium bicarbonate, hypoxanthine, thymidine, sodium pyruvate, L-glutamine, trace elements, growth factors, and phenol red reduced to 1.1 mg/L; Luciferase Assay Reagent (in reconstituted form) is an aqueous composition containing 20 mM tricine, 1.07 mM $(MgCO_3)_4Mg(OH)_2 \cdot 5H_2O$, 2.67 mM $MgSO_4$, 0.1 mM EDTA, 33.3 mM DTT, 270 μM coenzyme A, 470 μM luciferin, 530 μM ATP, having a final pH of 7.8.

AD-5075 has the following structure:

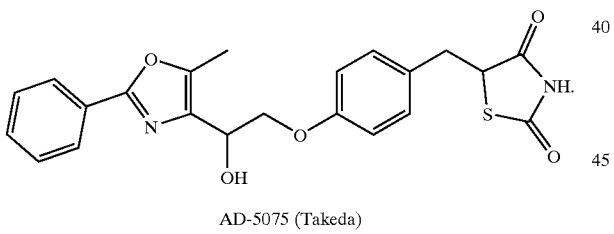

AD-5075 (Takeda)

Opti MEM 1 Reduced-Serum Medium, alpha MEM, G418, and Lipofectamine are commercially available from GibcoBRL Life Technologies, Gaithersburg, Md. Alpha MEM is an aqueous composition having the following components:

| Component: Inorganic Salts | mg/L |
|---|---|
| $CaCl_2$ (anhyd.) | 200.00 |
| $CaCl_2 \cdot 2H_2O$ | — |
| KCl | 400.00 |
| $MgSO_4$ (anhyd.) | 97.67 |
| $MgSO_4 \cdot 7H_2O$ | — |
| NaCl | 6800.00 |
| $NaHCO_3$ | 2200.00 |
| $NaH_2PO_4 \cdot H_2O$ | 140.00 |
| $NaH_2PO_4 \cdot 2H_2O$ | — |

-continued

| | mg/L |
|---|---|
| Other Components: | |
| D-Glucose | 1000.00 |
| Lipoic Acid | 0.20 |
| Phenol Red | 10.00 |
| Sodium Pyruvate | 110.00 |
| Amino Acids: | |
| L-Alanine | 25.00 |
| L-Arginine.HCl | 126.00 |
| L-Asparagine.$H_2O$ | 50.00 |
| L-Aspartic Acid | 30.00 |
| L-Cystine | — |
| L-Cystine.2HCl | 31.00 |
| L-Cysteine HCl | — |
| L-Cysteine HCl.$H_2O$ | 100.00 |
| L-Glutamic Acid | 75.00 |
| L-Glutamine | 292.00 |
| L-Alanyl-L-Glutamine | — |
| Glycine | 50.00 |
| L-Histidine HCl.$H_2O$ | 42.00 |
| L-Isoleucine | 52.00 |
| L-Leucine | 52.00 |
| L-Lysine.HCl | 73.00 |
| L-Methionine | 15.00 |
| L-Phenylalanine | 32.00 |
| L-Proline | 40.00 |
| L-Serine | 25.00 |
| L-Threonine | 48.00 |
| L-Tryptophan | 10.00 |
| L-Tyrosine | — |
| L-Tyrosine (disodium salt) | 52.00 |
| L-Valine | 46.00 |
| Vitamins: | |
| L-Ascorbic acid | 50.00 |
| Biotin | 0.10 |
| D-Ca Pantothenate | 1.00 |
| Choline Chloride | 1.00 |
| Folic acid | 1.00 |
| i-Inositol | 2.00 |
| Niacinamide | 1.00 |
| Pyridoxal HCl | 1.00 |
| Riboflavin | 0.10 |
| Thiamine HCl | 1.00 |
| Vitamin $B_{12}$ | 1.40 |
| Ribonucleosides | |
| Adenosine | 10.00 |
| Cytidine | 10.00 |
| Guanosine | 10.00 |
| Uridine | 10.00 |
| Deoxyribonucleosides | |
| 2' Deoxyadenosine | 10.00 |
| 2' Deoxycytidine HCl | 11.00 |
| 2' Deoxyguanosine | 10.00 |
| Thymidine | 10.00 |

The instant compounds, which are useful for treating the above discussed disease states, will preferably have $IC_{50}$ values at one, two or all of the PPAR (PPARγ, PPARδ or PPARα) receptor sites of equal to or less than 10 μM in the binding assay, preferably, an $IC_{50}$ of 100 nM in the binding assay, and more preferably, the instant compounds have an $IC_{50}$ equal to or less than 50 nM in the binding assay. Most preferably, the instant compounds have an $IC_{50}$ equal to or less than 10 nM in the binding assay.

PPAR Receptor Binding Assay

A. Preparation of Human PPARγ2 and δ

Human PPARγ2 and PPARδ, independently, were prepared as gst-fusion proteins in *E. coli*. The full length human cDNA for PPARγ2 and PPARδ were subcloned into the PGEX-2T and PGEX-KT, respectively, expression vector (Pharmacia). *E. coli* containing the plasmid were grown, induced, and then harvested by centrifugation. The resuspended pellet was broken in a French press and debris was removed by centrifugation at 12,000×g. Receptors were purified from the supernatant by affinity chromatography on glutathione sepharose. After application to the column, and 1 wash, receptor was eluted with glutathione. Glycerol was added to stabilize the receptor and aliquots were frozen at −80° C. for later use.

B. [$^3$H]AD-5075 and Example 11 Displacement Assay for PPARγ2 and PPARδ, respectively For each assay, an aliquot of receptor (1:1000–1:3000 dilution) was incubated in TEGM (10 mM Tris, pH 7.2, 1 mM EDTA, 10% glycerol, 7 μl/100 ml β-mercaptoethanol, 10 mM Na molybdate, 1 mM dithiothreitol, 5 μg/ml aprotinin, 2 μg/ml leupeptin, 2 μg/ml benzamide and 0.5 mM PMSF) containing 5–10% COS-1 cell cytoplasmic lysate and 10 nM labeled thiazolidinedione ([$^3$H$_2$]AD-5075, 21 Ci/mmole), ±test compound compound, [$^3$H$_2$]Example 11, 17 Ci/mmole), ±test compound, respectively. Assays were incubated for ~16 h at 4° C. in a final volume of 300 μl. Unbound ligand was removed by addition of 200 μl dextran/gelatin-coated charcoal, on ice, for ~10 minutes. After centrifugation at 3000 rpm for 10 min at 4° C., 200 μl of the supernatant fraction was counted in a liquid scintillation counter. In this assay the $K_D$ for AD-5075 and Example 11 is ≈1 nM, respectively.

III. In Vivo Studies

Methods db/db Mice are obese, highly insulin resistant animals. The db locus has been shown to code for the leptin receptor. These animals are substantially hypertriglyceridemic and hyperglycemic.

Male db/db mice (10–11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, Cholesterol and triglyceride concentrations were determined from blood obtained by tail bleeds at 3–5 day intervals during the study period. Glucose, cholesterol and triglyceride, determinations were performed on a Boehringer Mannheim Hitachi 911 automatic analyzer (Boehringer Mannheim, Indianapolis, Ind.) using heparinized plasma diluted 1:5, or 1:6 (v/v) with normal saline. Lean animals were age-matched heterozygous mice maintained in the same manner. The instant compounds were found to lower triglyceride and glucose levels at a dose of about 100 mg/kg, preferably a dose of about 10–50 mg/kg, when administered by oral gavage daily for a period of at least 5 days.

Lipoprotein analysis was performed on either serum, or EDTA treated plasma obtained by heart puncture from anesthetized animals at the end of the study. Apolipoprotein concentrations were determined by ELISA, and cholesterol particles were analyzed by FPLC, precipitation, or ultracentrifugation. Total liver RNA was prepared from tissue that had been frozen on liquid nitrogen at the time of euthanasia. Apolipoprotein mRNA was analyzed on Northern Blots using specific probes for mouse or rat proteins.

What is claimed is:

1. A compound having the formula I or Ia:

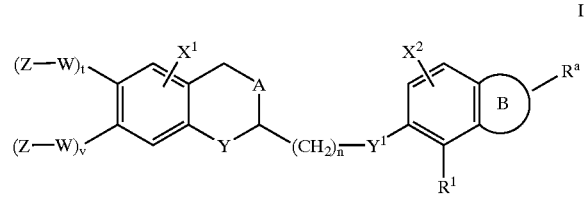

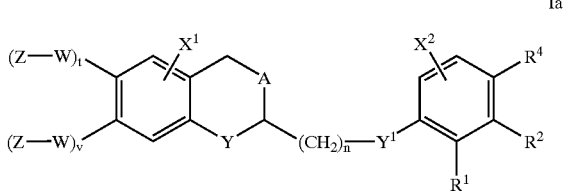

or a pharmaceutically acceptable salt thereof, wherein:

A is a single or double bonded carbon or a single or double bond;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^2$ is selected from a group consisting of: H, $C_{1-15}$ alkyl, $C_{2-15}$ alkenyl, $OR^3$, $CO_2$alkyl, COalkyl, OH, —OC(O)$R^3$, $C_{2-15}$ alkynyl, $C_{5-10}$ aryl, and $C_{5-10}$ heteroaryl, wherein said heteroaryl is selected from the group consisting of tetrazole, benzothiophene, and benzofuran, said alkyl, alkenyl, alkynyl, aryl and heteroaryl optionally substituted with 1 to 3 groups of $R^a$;

$R^3$ is selected from a group consisting of: H, $NHR^1$, NHacyl, $C_{1-15}$ alkyl, $C_{2-15}$ alkenyl, $C_{1-15}$ alkoxy, $CO_2$alkyl, OH, $C_{2-15}$ alkynyl, $C_{5-10}$ aryl, and $C_{5-10}$ heteroaryl, wherein said heteroaryl is selected from the group consisting of tetrazole, benzothiophene, and benzofuran, said alkyl, alkenyl, alkynyl, aryl and heteroaryl optionally substituted with 1 to 3 groups of $R^a$;

$R^4$ is selected from the group consisting of: $R^2$, —D—$R^5$ and

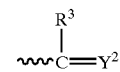

$R^5$ is selected from the group consisting of: $C_{5-10}$ aryl and $C_{5-10}$ heteroaryl, wherein said heteroaryl is selected from the group consisting of tetrazole, benzothiophene, and benzofuran, said aryl and heteroaryl optionally substituted with 1 to 3 groups of $R^a$;

W is —$CR^6R^7$—, or

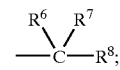

$R^8$ is selected from the group consisting of $CR^6R^7$, O, $NR^6$, and $S(O)_P$;

$R^6$ and $R^7$ are independently selected from the group consisting of H and $C_{1-6}$ alkyl;

B is a 5 membered heterocycle containing 1 double bond and 1 heteroatom selected from the group consisting of O and S, wherein said heterocycle and the aromatic ring to which it is fused represent benzothiophene or benzofuran, the heterocycle being optionally unsubstituted or substituted with 1 to 3 groups of $R^a$;

D is selected from the group consisting of: O, S(O)p and $NR^1$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $C_{5-10}$ aryl, $C_{5-10}$ aralkyl, $C_{5-10}$ heteroaryl and $C_{2-10}$ acyl, wherein said heteroaryl is selected from the group consisting of tetrazole, benzothiophene, and benzofuran, said alkyl, alkenyl, alkynyl, aryl and heteroaryl optionally substituted with 1 to 3 groups of $R^a$;

$R^a$ represents a member selected from the group consisting of: halo, aryl, heteroaryl, $CF_3$, $OCF_3$, CN, $NO_2$, $R^3$, $OR^3$; $SR^3$, $S(O)R^3$, $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, and $OCON(R^3)_2$, wherein said heteroaryl is selected from the group consisting of tetrazole, benzothiophene, and benzofuran and said aryl and heteroaryl are optionally substituted with 1 to 3 groups of halo or C1–6 alkyl;

Y is selected from the group consisting of: S, —$CH_2$—, CO, and O with the proviso that if A is a single or double bonded carbon or a single bond, Y is —$CH_2$— or CO;

$Y^2$ is selected from the group consisting of: O, $N(C_{1-15})$ alkyl, $N(CO_2)$alkyl, N—Oalkyl, N—Oacyl and N—OH, with the proviso that if $Y^2$ is O and $R^3$ is $CH_3$ then n is 2;

$Y^1$ is selected from the group consisting of: O, NH, $S(O)_p$ and $CH_2$;

Z is selected from the group consisting of: $CO_2R^3$, $CONHSO_2Me$, $CONH_2$ and 5-(1H-tetrazole); or $(Z—W)_t$ or $(Z—W)_v$ together with $X^1$ can form a 5 or 6 membered ring, said ring being a carbocycle, optionally substituted with 1 to 3 groups of $R^a$; in the case where $(Z—W)_t$ is used v is 0 or 1; in the case where $(Z—W)_v$ is used t is 0 or 1;

t and v are independently 0 or 1 such that t+v=1;

n is 2–4;

p is 0–2; and at least one heteroaryl substituent or the combination of B and the aromatic ring to which B is fused or the bicyclic structure on the left side of formula 1 or 1a is benzofuran.

2. A compound represented by formula I or Ia:

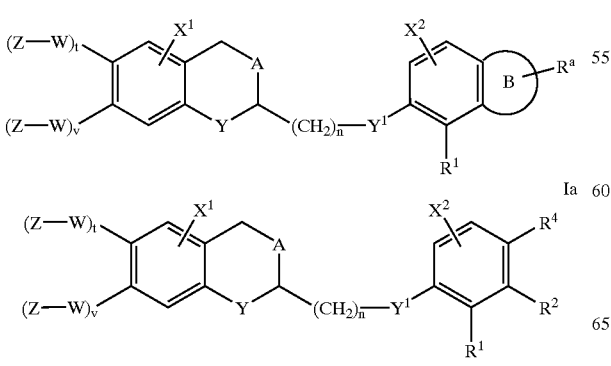

or a pharmaceutically acceptable salt thereof, wherein:

A represents a single or double bonded carbon, or a direct single or double bond;

Y represents a member selected from the group consisting of: S, —$CH_2$—, —C(O)—, and —O—, with the proviso that if A represents a single or double bonded carbon or a single bond, Y is —$CH_2$— or —C(O)—;

one of t and v is zero and the other is 1;

W is

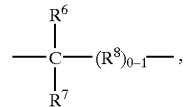

and

Z is selected from the group consisting of: $CO_2R^{3'}$, $CONHSO_2C_{1-6}$ alkyl, $CONH_2$ and 5-(1H-tetrazolyl); or in the alternative, one of $(Z—W)_t$ and $(Z—W)_v$ is taken in combination with $X^1$ to represent a 5 or 6 membered fused ring, said ring being a carbocycle, optionally substituted with 1 to 3 $R^a$ groups;

when $(Z—W)_t$ is taken in combination with $X^1$, v is 0 or 1, and when $(Z—W)_v$ is taken in combination with $X^1$, t is 0 or 1;

$X^1$ and $X^2$ are independently selected from a group consisting of: H, OH, $C_{1-15}$ alkyl, $C_{2-15}$ alkenyl, $C_{2-15}$ alkynyl, halo, $C_{5-10}$ aryl, $C_{5-10}$ heteroaryl, $C_{2-10}$ acyl, $C_{1-5}$ alkoxy, $C_{5-10}$ aryloxy, $C_{2-15}$ alkenyloxy, $C_{2-15}$ alkynyloxy, heteroaryloxy, and $C_{2-10}$ acyloxy, wherein said heteroaryl is selected from the group consisting of tetrazole, benzothiophene, and benzofuran, said alkyl, alkenyl, alkynyl, aryl, acyl and heteroaryl, and the alkyl, alkenyl, alkynyl, aryl, acyl and heteroaryl portions of alkoxy, aryloxy, alkenyloxy, alkynyloxy, heteroaryloxy and acyloxy being optionally substituted with 1 to 3 $R^a$ groups;

n is 2, 3 or 4;

$Y^1$ represents O, NH, $CH_2$ or $S(O)_p$;

p is 0, 1 or 2;

B represents a 5 or 6 membered fused ring containing 0 to 2 double bonds, and optionally containing 1 heteroatom selected from the group consisting of O and S, with the proviso that when B is a heterocycle, said heterocycle and the aromatic ring to which it is fused represent benzothiophene, or benzofuran, said ring being optionally substituted with 1 to 3 $R^a$ groups;

$R^1$ is selected from a group consisting of: H, $C_{1-15}$ alkyl, $C_{2-15}$ alkenyl and $C_{2-15}$ alkynyl, said alkyl, alkenyl and alkynyl being optionally substituted with 1 to 3 $R^a$ groups;

$R^2$ is selected from a group consisting of: H, OH, $C_{1-15}$ alkyl, $C_{2-15}$ alkenyl, $C_{2-15}$ alkynyl, $C_{5-10}$ aryl, $C_{5-10}$ heteroaryl, —$C(O)C_{1-15}$ alkyl, $CO_2C_{1-6}$ alkyl, —OC(O)$R^{3'}$, $C_{1-6}$ alkoxy, $C_{5-10}$ aryloxy, $C_{2-15}$ alkenyloxy, $C_{2-15}$ alkynyloxy, heteroaryloxy and $C_{2-10}$ acyloxy, wherein said heteroaryl and the heteroaryl portion of heteroaryloxy are selected from the group consisting of tetrazole, benzothiophene, and benzofuran, said alkyl, alkenyl, alkynyl, aryl and heteroaryl, and the alkyl, aryl, alkenyl, alkynyl, heteroaryl and acyl portions of alkoxy, aryloxy, alkenyloxy, alkynyloxy, heteroaryloxy and acyloxy being optionally substituted with 1 to 3 $R^a$ groups;

47

$R^3$ is selected from a group consisting of: H, OH, $NHR^1$, NHacyl, $C_{1-5}$ alkyl, $C_{2-15}$ alkenyl, $C_{1-15}$ alkoxy, $CO_2$alkyl, $C_{2-15}$ alkynyl, $C_{5-10}$ aryl, and $C_{5-10}$ heteroaryl wherein said heteroaryl is selected from the group consisting of tetrazole, benzothiophene, and benzofuran, said alkyl, alkenyl, alkynyl, aryl and heteroaryl optionally substituted with 1 to 3 $R^a$ groups;

each $R^a$ independently represents a member selected from the group consisting of: $R^{3'}$, halo, $CF_3$, $OCF_3$, CN, $NO_2$, $OR^{3'}$, $S(O)_p—R^{3'}$; $N(R^{3'})_2$, $NR^{3'}COR^{3'}$, $NR^{3'}CO_2R^{3'}$, $NR^{3'}CON(R^{3'})_2$, $NR^{3'}SO_2R^{3'}$, $C(O)R^{3'}$, $CO_2R^{3'}$, $CON(R^{3'})_2$, $SO_2N(R^{3'})_2$, and $OCON(R^{3'})_2$, and when $R^{3'}$ is present and represents alkyl, alkenyl, alkynyl, aryl or heteroaryl, said alkyl, alkenyl, alkynyl, aryl or heteroaryl group is optionally substituted with 1 to 3 halo, hydroxy, $C_{1-3}$ alkoxy, carboxy or amino groups, and when at least two $R^a$ groups are present, they may also be taken in combination with any intervening atoms to represent a 4–6 membered ring, said ring containing no heteroatoms, and said ring being optionally interrupted by 1–2 —C(O)— groups, and optionally substituted with 1–3 halo, hydroxy, $C_{1-6}$ alkyl or amino groups;

$R^{3'}$ represents H, $C_{1-6}$ alkyl, $C_{2-6}$ alkenyl, $C_{2-6}$ alkynyl, aryl or heteroaryl wherein said heteroaryl is selected from the group consisting of tetrazole, benzothiophene, and benzofuran;

$R^4$ represents $R^2$, —D—$R^5$ or

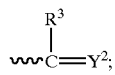

D is selected from O, S(O)p, $NR^1$ and $CR^6R^7$;

$R^5$ is selected from the group consisting of: $C_{5-10}$ aryl and $C_{5-10}$ heteroaryl, wherein said heteroaryl is selected from the group consisting of tetrazole, benzothiophene, and benzofuran, said aryl and heteroaryl being optionally substituted with 1 to 3 $R^a$ groups;

$Y^2$ is selected from the group consisting of: O, $N(C_{1-15})$ alkyl, $N(CO_2)$alkyl, N—Oalkyl, N—Oacyl and N—OH, with the proviso that if $Y^2$ is O and $R^3$ is $CH_3$ then n is 2;

$R^8$ is optional and is selected from the group consisting of $CR^6R^7$, O, $NR^6$ and $S(O)_p$, $R^6$ and $R^7$ are independently selected from H and $C_{1-6}$ alkyl; and at least one heteroaryl substituent or the combination of B and the aromatic ring to which B is fused or the bicyclic structure on the left side of formula 1 or 1a is benzofuran.

3. A compound of claim 1 where $X^1$ and $X^2$ are independently H or halo.

4. A compound of claim 1 where Y is O.

5. A compound of claim 1 where Y is $S(O)_p$, wherein p is 0–2.

6. A compound of claim 1 where Y is —$CH_2$—.

7. A compound of claim 1 where Y is —CO—.

8. A compound of claim 1 where A is a single or double bonded carbon.

9. A compound of claim 1 where A is a single or double bond.

10. A compound of claim 1 having the formula I where B is a 5 membered heterocycle, wherein said heterocycle and the aromatic ring to which it is fused represent

48 benzothiophene, or benzofuran, the heterocycle being optionally unsubstituted or substituted with 1 to 3 groups of $R^a$.

11. A compound of claim 1 where $R^4$ is selected from the group consisting of: $R^2$, —D—$R^5$ or

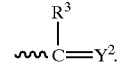

12. A compound of claim 1 wherein: $(Z—W)_t$ or $(Z—W)_v$ together with $X^1$ forms a 5 or 6 membered ring, said ring being a carbocycle, optionally substituted with 1 to 3 groups of $R^a$; A is a double bond; Y is O; in the case where $(Z—W)_t$ is used v is 0 or 1; in the case where $(Z—W)_v$ is used t is 0 or 1; and all other variables are described as above.

13. A compound of claim 1 wherein $R^1$ is H or $C_{1-15}$ alkyl;

$X^1$ and $X^2$ are independently H, or halo;

B is a 5 membered heterocycle, wherein the combination of B and the aromatic ring to which B is fused is benzofuran, the heterocycle being optionally unsubstituted or substituted with 1 to 3 $R^a$ groups;

A is a double bond;

Y is O or S;

$Y^1$ is O;

W is —$CR^6R^7$—;

$R^a$ is a member selected from the group consisting of: halo, aryl, heteroaryl, $CF_3$, $OCF_3$, CN, $NO_2$, $R^{3'}$, $OR^{3'}$; $SR^{3'}$, $S(O)R^{3'}$, $SO_2R^{3'}$, $NR^{3'}COR^{3'}$, $COR^{3'}$, $CON(R^{3'})_2$, and $SO_2N(R^{3'})_2$, wherein said heteroaryl is selected from the group consisting of tetrazole, benzothiophene, and benzofuran, said aryl and heteroaryl optionally substituted with 1 to 3 halo or C1–6 alkyl groups;

$R^{3'}$ represents H, $C_{1-6}$ alkyl, $C_{2-6}$ alkenyl, $C_{2-6}$ alkynyl, aryl or heteroaryl, wherein said heteroaryl is selected from the group consisting of tetrazole, benzothiophene, and benzofuran; and Z is $CO_2R^{3'}$, $CONHSO_2Me$, $CONH_2$ or 5-(1H-tetrazole).

14. A compound of claim 1 wherein:

$R^1$ is H or $C_{1-15}$ alkyl;

$X^1$ and $X^2$ are independently H, or halo;

A is a double bond;

$R^4$ is selected from the group consisting of: $R^2$, —D—$R^5$ or

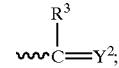

Y is O or S;

$Y^1$ is O;

W is —$CR^6R^7$—;

$R^a$ is a member selected from the group consisting of: halo, aryl, heteroaryl, $CF_3$, $OCF_3$, CN, $NO_2$, $R^{3'}$, $OR^{3'}$; $SR^{3'}$, $S(O)R^{3'}$, $SO_2R^{3'}$, $NR^{3'}COR^{3'}$, $COR^{3'}$, $CON(R^{3'})_2$, and $SO_2N(R^{3'})_2$, wherein said heteroaryl is selected from the group consisting of tetrazole, benzothiophene, and benzofuran, said aryl and heteroaryl optionally substituted with 1 to 3 halo or C1–6 alkyl groups;

$R^{3'}$ represents H, $C_{1-6}$ alkyl, $C_{2-6}$ alkenyl, $C_{2-6}$ alkynyl, aryl or heteroaryl, wherein said heteroaryl is selected from the group consisting of tetrazole, benzothiophene, and benzofuran; and Z is $CO_2R^{3'}$, $CONHSO_2Me$, $CONH_2$ or 5-(1H-tetrazole).

15. A compound of claim 1 wherein:

R¹ is $C_{1-15}$ alkyl;

R⁴ is —D—R⁵ or

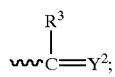

X² is H, or halo;

A is a double bond;

Y is O or S;

Y¹ is O;

R$^a$ is a member selected from the group consisting of: halo, aryl, heteroaryl, $CF_3$, $OCF_3$, CN, $NO_2$, R³', OR³'; SR³', S(O)R³', $SO_2$R³', NR³'COR³', COR³', CON(R³')$_2$, and $SO_2$N(R³')$_2$, wherein said heteroaryl is selected from the group consisting of tetrazole, benzothiophene, and benzofuran, said aryl and heteroaryl optionally substituted with 1 to 3 halo or C1–6 alkyl groups;

R³' represents H, $C_{1-6}$ alkyl, $C_{2-6}$ alkenyl, $C_{2-6}$ alkynyl, aryl or heteroaryl, wherein said heteroaryl is selected from the group consisting of tetrazole, benzothiophene, and benzofuran, (Z—W)$_t$ or (Z—W)$_v$ together with X¹ forms a 5 or 6 membered ring, said ring being a carbocycle, optionally substituted with 1 to 3 groups of R$^a$; in the case where (Z—W)$_v$ is used v is 0 or 1; in the case where (Z—W)$_v$ is used t is 0 or 1; and all other variables are as described above.

16. A compound according to claim 1 represented by one of the following structural formulas:

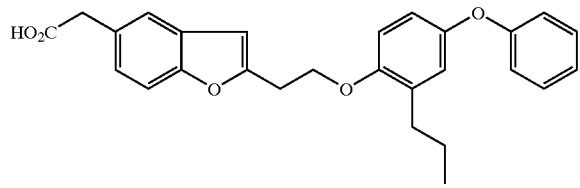

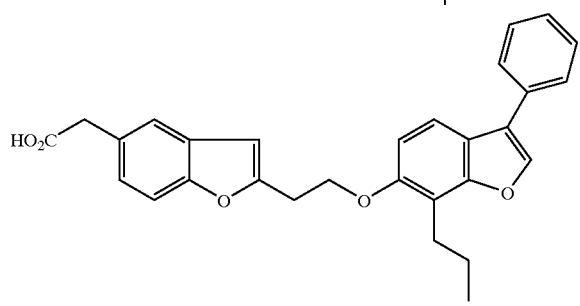

and

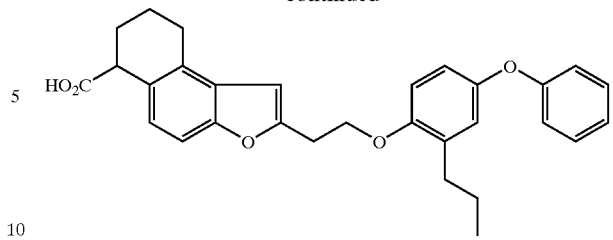

or a salt, ester or hydrate thereof.

17. A compound in accordance with claim 1 selected from the group consisting of:

2-(2-(3-Phenyl-7-propylbenzofuran-6-yloxy)ethyl) benzothiophen-5-acetic acid;

2-(2-(3-Neopentyl-7-propylbenzofuran-6-yloxy)ethyl) benzofuran-5-acetic acid;

2-(2-(4-Phenoxy-2-propylphenoxy)ethyl)benzofuran-5-acetic acid;

2-(2-(3-Phenyl-7-propylbenzofuran-6-yloxy)ethyl)-benzofuran-5-acetic acid;

2-(2-(4-Phenoxy-2-propylphenoxy)ethyl-4,5,6,7-tetrahydronaphtho[2,1-b]furan-7-carboxylic acid;

or a salt or hydrate thereof.

18. A compound according to claim 17 which is:

2-(2-(4-Phenoxy-2-propylphenoxy)ethyl)-4,5,6,7-tetrahydronaphtho[2,1-b]furan-7-carboxylic acid or a salt or hydrate thereof.

19. A pharmaceutical composition which is comprised of a compound as described in claim 2 in combination with a carrier.

20. A pharmaceutical composition which comprises an inert carrier and a compound of claim 1.

21. A pharmaceutical composition in accordance with claim 19 which is further comprised of at least one member selected from the group consisting of: a sulfonylurea, fibrate, HMG-CoA reductase inhibitor, beta-sitosterol inhibitor, cholesterol acyltransferase inhibitor, biguanide, cholestyramine, angiotensin II antagonist, melinamide, nicotinic acid, fibrinogen receptor antagonist, aspirin, α-glucosidase inhibitor, insulin secretagogue and insulin.

22. A pharmaceutical composition which comprises an inert carrier and a compound of claim 1, in combination with a sulfonylurea, fibrate, HMG-CoA reductase inhibitor, beta-sitosterol inhibitor, cholesterol acyltransferase inhibitor, biguanide, cholestyramine, angiotensin II antagonist, melinamide, nicotinic acid, fibrinogen receptor antagonist, aspirin, α-glucosidase inhibitor, insulin secretagogue or insulin.

23. A pharmaceutical composition which comprises an inert carrier and a compound of claim 1, in combination with fenfluramine, dexfenfluramine, phentermine or a β₃ adrenergic receptor agonist.

* * * * *